US012606783B2

(12) United States Patent
Chung et al.

(10) Patent No.: US 12,606,783 B2
(45) Date of Patent: *Apr. 21, 2026

---

(54) WELL PLATE AND 3D CULTURE PLATE COMPRISING THE SAME

(71) Applicant: NEXT & BIO INC., Seoul (KR)

(72) Inventors: Seok Chung, Seoul (KR); Ji Hoon Yang, Seoul (KR); Kyu Hwan Na, Busan (KR); Ye Si Jun, Seoul (KR); Yong Hun Jung, Seoul (KR)

(73) Assignee: NEXT & BIO INC., Seoul (KR)

( * ) Notice: Subject to any disclaimer, the term of this patent is extended or adjusted under 35 U.S.C. 154(b) by 549 days.

This patent is subject to a terminal disclaimer.

(21) Appl. No.: 18/115,985

(22) Filed: Mar. 1, 2023

(65) Prior Publication Data

US 2023/0272320 A1 Aug. 31, 2023

Related U.S. Application Data

(63) Continuation-in-part of application No. 17/628,710, filed as application No. PCT/KR2020/008271 on Jun. 25, 2020, now Pat. No. 12,540,308.

(51) Int. Cl.
*C12M 1/32* (2006.01)

(52) U.S. Cl.
CPC .................................... *C12M 23/12* (2013.01)

(58) Field of Classification Search
CPC .............................. C12M 23/12; C12M 25/14
See application file for complete search history.

(56) References Cited

U.S. PATENT DOCUMENTS

| | | | |
|---|---|---|---|
| 7,767,154 B2 | 8/2010 | Nichols et al. | |
| 8,642,339 B2 | 2/2014 | Sato et al. | |
| 9,922,421 B1 | 3/2018 | Degani | |
| 2009/0010507 A1 | 1/2009 | Geng | |
| 2011/0003389 A1 | 1/2011 | Nakazawa et al. | |
| 2011/0311144 A1 | 12/2011 | Tardif | |
| 2013/0135292 A1 | 5/2013 | Lee | |
| 2013/0174287 A1 | 7/2013 | Higuera | |
| 2015/0232673 A1 | 8/2015 | Jing | |

(Continued)

FOREIGN PATENT DOCUMENTS

| | | |
|---|---|---|
| CN | 102257123 A | 11/2011 |
| CN | 106459925 A | 2/2017 |

(Continued)

OTHER PUBLICATIONS

Chung, Seok, Ji Hoon Yang, Kyu Hwan Na, Yong Hun Jung "Brain Organoid Manufacturing Method". U.S. Appl. No. 17/629,034, filed Jan. 21, 2022 (Year: 2022).*

(Continued)

*Primary Examiner* — Michael L Hobbs
(74) *Attorney, Agent, or Firm* — Jason A. Smith; Shumaker, Loop & Kendrick, LLP

(57) ABSTRACT

A well plate and a 3D cell culture plate are described. The well plate having a repeating pattern. The wells of the well plate is continuously provided with a space part in between a main well to be injected with culture solution and a sub well including a recessed part where the cells are cultured. The main well of the well plate is connected to the space part with forming a step, and the sub well is connected to the part with forming an inclined surface.

13 Claims, 19 Drawing Sheets

(56) References Cited

U.S. PATENT DOCUMENTS

| | | | |
|---|---|---|---|
| 2017/0081625 A1* | 3/2017 | Wikswo | C12M 41/48 |
| 2017/0253844 A1 | 9/2017 | Fang et al. | |
| 2018/0187136 A1 | 7/2018 | Lichtenberg et al. | |
| 2018/0255240 A1 | 9/2018 | Kato | |
| 2019/0001046 A1 | 1/2019 | Matheu | |
| 2019/0194611 A1 | 6/2019 | Jo et al. | |
| 2019/0258846 A1 | 8/2019 | Dinov | |
| 2020/0017811 A1* | 1/2020 | Apfel | C12M 21/08 |
| 2020/0217462 A1 | 7/2020 | Mitsuzuka | |
| 2020/0300750 A1 | 9/2020 | Eshel | |
| 2021/0272378 A1 | 9/2021 | Stomakhin | |
| 2022/0275328 A1 | 9/2022 | Chung et al. | |

FOREIGN PATENT DOCUMENTS

| | | | |
|---|---|---|---|
| CN | 108456642 A | 8/2018 | |
| CN | 111337775 A | 6/2020 | |
| EP | 2173853 B1 | 4/2010 | |
| EP | 3150704 A1 | 4/2017 | |
| EP | 3129144 B1 | 2/2019 | |
| JP | 2011167101 A | 9/2011 | |
| JP | 2012157267 A | 8/2012 | |
| JP | 2017506066 A | 3/2017 | |
| KR | 2019790001973 Y1 | 11/1979 | |
| KR | 20100088297 A | 8/2010 | |
| KR | 20130013537 A | 2/2013 | |
| KR | 20140113139 A | 9/2014 | |
| KR | 20160017036 A | 2/2016 | |
| KR | 20160115764 A | 10/2016 | |
| KR | 20160117631 A | 10/2016 | |
| KR | 20170003177 A | 1/2017 | |
| KR | 20170010857 A | 2/2017 | |
| KR | 20170040442 A | 4/2017 | |
| KR | 20170056241 A | 5/2017 | |
| KR | 20170073696 A | 6/2017 | |
| KR | 20180115236 A | 10/2018 | |
| KR | 20180136410 A | 12/2018 | |
| KR | 20200081295 A | 7/2019 | |
| KR | 20200051481 A | 5/2020 | |
| KR | 20200081294 A | 7/2020 | |
| WO | 2013/047655 A1 | 4/2013 | |
| WO | 2014196204 A1 | 12/2014 | |
| WO | 2015/182159 A | 12/2015 | |
| WO | 2015182159 A1 | 12/2015 | |
| WO | 2016069917 A1 | 5/2016 | |
| WO | 2016/103002 A1 | 6/2016 | |
| WO | 2016203748 A1 | 12/2016 | |
| WO | 2017060884 A1 | 4/2017 | |
| WO | 2018011558 A1 | 1/2018 | |
| WO | 2018196472 A1 | 11/2018 | |
| WO | 2019/145847 A1 | 8/2019 | |
| WO | 2019/203255 A1 | 10/2019 | |

OTHER PUBLICATIONS

European Search Report (ESR) for EP Pat. App. 20941637.9 mailed Feb. 26, 2024 (17 pages).
English translation of JP Office Action ("JP OA") for JP Pat. App. 2023-053903 mailed May 7, 2024 (4 pages).
English translation of JP Office Action ("JP OA") for JP Pat. App. 2022-580485 mailed May 21, 2024 (3 pages).
English translation of CN Office Action ("CN OA") for CN Pat. App. 202080057825.0 mailed Nov. 29, 2024 (9 pages).
English translation of JP Office Action ("JP OA") for JP Pat. App. 2022-58053 mailed Jul. 2, 2024 (4 pages).
English translation of JP Office Action ("JP OA") for JP Pat. App. 2022-580506 mailed Mar. 12, 2024 (5 pages).
English translation of JP Office Action ("JP OA") for JP Pat. App. 2022-580503 mailed Jan. 7, 2025 (2 pages).
Non-Final Office Action (NFOA) for U.S. Appl. No. 17/628,719, mailed Mar. 3, 2025 (16 pages).
Restriction Requirement for U.S. Appl. No. 17/628,710, mailed Dec. 3, 2024 (7 pages).
Anonymous: "GravityPLUS(TM) Hanging" Dec. 31, 2015.
Sebastien Sart et al. "Three-Dimensional Aggregates", Tissue Engineering Part B, vol. 20, No. 5 (Oct. 1, 2014) p. 365-380.
Mark D Ungrin et al. "Rational bioprocess design" Biotechnology and Bioengineering, John Wiley, Hoboken USA vol. 109, No. 4, p. 853-866 (Dec. 2, 2011).
Tomomi G. Otsuji et al. "A 3D Sphere Culture System" Stem Cell Reports, vol. 2, No. 5. p. 734-745 (May 1, 2014).
SCREEN Application Note vol. 2, Jun. 2017, URL <http://screen-cell3imager.com/assets/pdf/application/rm/rm-4.pdf>, Searched on May 14, 2024.
Apr. 7, 2025 Non-Final Rejection issued in U.S. Appl. No. 17/629,034.
Amin ND, Pasca SP. Building Models of Brain Disorders with Three-Dimensional Organoids. Neuron. Oct. 24, 2018;100 (2):389-405.
Comley, John. "Spheroids." Drug Discovery (2017): 31.
Lancaster MA, Renner M, Martin CA, Wenzel D, Bicknell LS, Hurles ME, Homfray T, Penninger JM, Jackson AP, Knoblich JA. Cerebral organoids model human brain development and microcephaly. Nature. Sep. 19, 2013;501 (7467):373-9. doi: 10.1038/ nature12517. Epub Aug. 28, 2013. PMID: 23995685; PMCID: PMC3817409. (Year: 2013).
Non-Final Office Action Issued in Corresponding U.S. Appl. No. 17/628,710 on May 1, 2025 (13 Pages).
Kazutoshi Takahashi et al. "Induction of Pluripotent Stem Cells from Mouse Embryonic and Adult Fibroblast Cultures by Defined Factors", Cell, vol. 126, p. 663-676, Aug. 25, 2006.
Kazutoshi Takahashi et al. "Induction of Pluripotent Stem Cells from Adult Human Fibroblasts by Defined Factors", Cell, vol. 131, p. 861-872, Nov. 30, 2007.
Yuguo Lei et al. "A fully defined and scalable 3D culture system for human pluripotent stem cell expansion and differentiation", PNAs, p. E5039-E5048, published online Nov. 18, 2013; accessed at www.pnas.org/cgi/doi/10.1073/pnas.1309408110.
M. Lancaster et al. "Generation of cerebral organoids from human pluripotent stem cells", Natural Protocols, vol. 9, No. 10, p. 2329-2340, Sep. 4, 2014.
International Search Report for PCT/KR2020/008242 mailed Mar. 24, 2021 (6 pages).
International Search Report for PCT/KR2020/008271 mailed Mar. 23, 2021 (5 pages).
International Search Report for PCT/KR2020/008274 mailed Mar. 23, 2021 (6 pages).
International Search Report for PCT/KR2020/008280 mailed Mar. 24, 2021 (6 pages).
International Search Report for PCT/KR2020/008285 mailed Mar. 24, 2021 (6 pages).
Non-Final Office Action Issued in Corresponding U.S. Appl. No. 17/628,719 on May 12, 2025 (32 Pages).
Chinese Office Action dated Mar. 8, 2024.
Non-Final Office Action Issued on Aug. 13, 2025 in Related U.S. Appl. No. 18/577,140 (11 Pages).
Non-Final Office Action Issued on Aug. 26, 2025 in Related U.S. Appl. No. 17/628,719 (17 Pages).
English translation of KR Office Action ("KR OA") for KR App. No. 10-2021-0090432 mailed Apr. 23, 2024 (7 pages).
Michele Zanoni et al. "Modeling neoplastic disease wiht spheroids and organoids" Journal of Hematology & Oncology, 13:97 (2020) (15 pages).
Written Opinion (WO) for PCT/KR2022/006454 mailed Aug. 17, 2022 (6 pages).
International Preliminary Report on Patentability for PCT/KR2022/006454 dated Dec. 14, 2023 (8 pages).
International Search Report for PCT/KR2022/006454 mailed Aug. 17, 2022 (7 pages).
Wayne Lewis "Artificial Intelligence Converts 2D Images Into 3D Using Deep Learning" [Video]. SciTech Daily. Nov. 9, 2019 (9 pages).
Kh Tohidul Islam et al., "A deep learning based framework for the registration of three dimensional multi-modal medical images of the head." Scientific Reports. Jan. 21, 2021 (13 pages).
Written Opinion (WO) for PCT/KR2021/095129 mailed Apr. 8, 2022 (8 pages).

(56)        References Cited

OTHER PUBLICATIONS

International Search Report for PCT/KR2021/095129 mailed Apr. 8, 2022 (5 pages).
Non-Final Office Action for U.S. Appl. No. 18/577,155 issued on Sep. 11, 2025 (22 Pages).

* cited by examiner

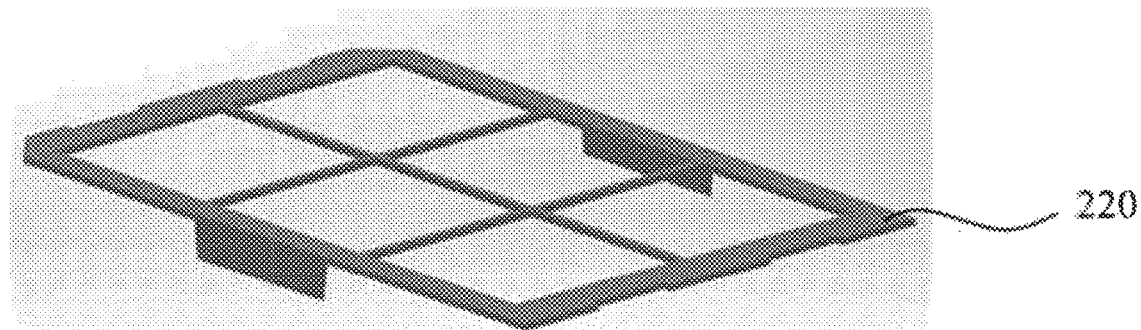
220
FIG. 3A
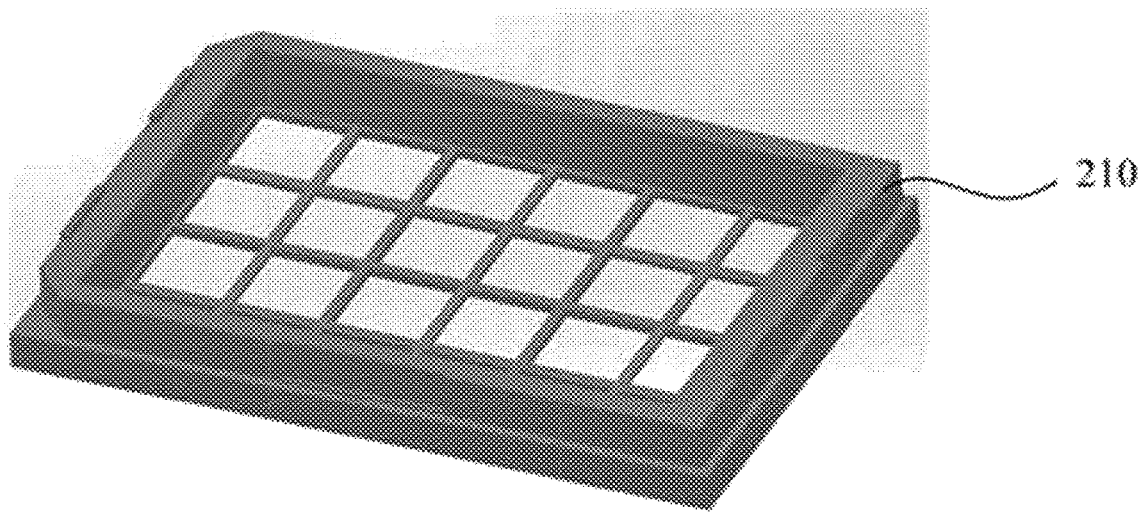
210
FIG. 3B
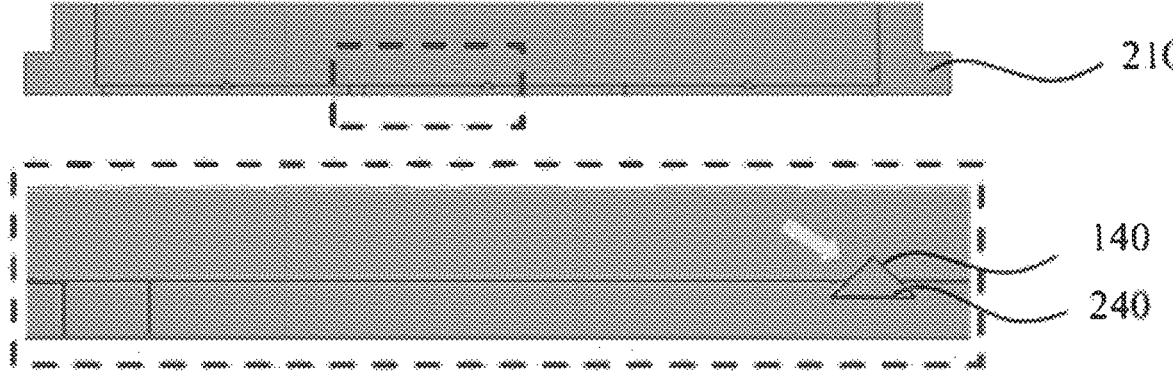
210
140
240
200: 210, 220                    FIG. 3C

2D iPSC 3D iPSC

WELL PLATE AND 3D CULTURE PLATE COMPRISING THE SAME

TECHNICAL FIELD

The present invention relates to a well plate and a 3D cell culture plate comprising the same. More specifically, the present invention relates to a well plate and a 3D cell culture plate comprising the same, for producing uniform-sized organoids.

BACKGROUND ART

A process of returning differentiated somatic cells to cells in an undifferentiated state (for example, stem cells) refers to reprogramming. Induced pluripotent stem cells (iPSCs) are also called reverse-differentiated stem cells and reverse-differentiated pluripotent stem cells, and reprogramming is the conversion of somatic cells into stem cells using reprogramming factors (Oct4, Klf4, Sox2, c-Myc, and the like) (Non-Patent Documents 1 and 2).

Induced pluripotent stem cells have a wide range of applications such as cell therapy agents, biotissue engineering, new drug development, toxicology, and precision medicine. These applications require culturing large amounts of high-efficiency and high-quality induced pluripotent stem cells and embryonic stem cells, and requires uniform-sized stem cells at the same efficiency, but in fact, research on this mass production technique is inadequate. Further, the efficiency of reprogramming induced pluripotent stem cells has also been quite low to date. Recently, many studies have been conducted on methods for clinical application, in other words, methods in which foreign genes are not integrated, in other words, DNA integration is not achieved, and among them, an attempt is made to produce induced pluripotent stem cells by a method such as an episomal vector, but this series of production methods have a problem in that the efficiency of the 3D culture method and the reprogramming efficiency of somatic cells are also low.

Moreover, for induced pluripotent stem cell reprogramming, the bottom of a 2D cell culture plate is coated with a hydrogel and used, but colonies are rarely formed, and even though colonies are formed after cell reprogramming, the colonies are not easily separated, which acts as a barrier not only to research purposes, but also to commercialization. In addition, since it is almost impossible to produce a large number of clones in the case of existing methods, it is difficult to stably secure clones in a state reprogrammed into induced pluripotent stem cells by the existing methods. Furthermore, there is also a need for a platform capable of easily screening induced pluripotent stem cells.

Meanwhile, Korean Patent No. 10-1756901 (Patent Document 1) discloses a cell culture chip capable of culturing 3D tissue cells. In the cell culture chip of Patent Document 1, a first culture part, a second culture part, and the third culture part are formed in each layer, and the degree of cell growth progress can be confirmed in each layer. However, the cell culture chip of Patent Document 1 has a problem in that spheroids and/or organoids cannot be obtained in high yield.

Further, there is a case where the pipetting work of replacing a culture solution during cell culture is performed, and in the case of a Corning spheroid microplate capable of 3D cell culture, spheroids or organoids in cell culture are affected, so that there is a problem which is not good for the cell culture environment because there is a case where the spheroids or organoids are sucked up or the positions thereof are changed during the pipetting work.

Matrigel (product name of BD Bioscience) is a protein complex extracted from sarcoma cells of Engelbreth-Holm-Swarm (EHS) mice, and contains an extracellular matrix (ECM) such as a laminin, collagen and a heparan sulfate proteoglycan, and a growth factor such as a fibroblast growth factor (FGF), an epiderma growth factor (EFG), an insulin-like growth factor (IGF), transforming growth factor-beta (TGF-$\beta$), and a platelet-derived growth factor (PDGF). The complex which forms Matrigel is utilized as a substrate for cell culture by providing a complex extracellular environment found in many tissues.

Since Matrigel is derived from mouse sarcoma, there is a high risk of transferring an immunogen and a pathogen. In addition, although Matrigel is used for cell growth and tissue formation, there is also criticism that there is a big problem with cell reproducibility because Matrigel is such a complex material. It is also unclear whether Matrigel simply acts as a passive 3D scaffold which provides a physical support for growing spheroids, or whether Matrigel actively affects spheroid formation by providing a biologically essential element. Furthermore, Matrigel is also expensive. Therefore, although Matrigel is a material which has contributed to the development of the cell culture technology field, there is also a fact that the development of the technology field is hindered by Matrigel.

Thus, the present inventors have conducted continuous studies on a technology of mass-culturing stem cells by enhancing the reprogramming efficiency of stem cells without using a hydrogel, thereby completing the present invention.

RELATED ART DOCUMENTS

Patent Document

1. Korean Patent No. 10-1756901

Non-Patent Documents

1. Takahashi K, Yamanaka S. Induction of pluripotent stem cells from mouse embryonic and adult fibroblast cultures by defined factors. Cell. 2006; 126:663-676.
2. Takahashi K, Tanabe K. Ohnuki M, Narita M, Ichisaka T, Tomoda K, Yamanaka S. Induction of pluripotent stem cells from adult human fibroblasts by defined factors. Cell. 2007; 131:861-872.

DISCLOSURE

Technical Problem

An object of the present invention is to provide a well plate and a 3D cell culture plate comprising the same.

However, a technical problem to be achieved by the present invention is not limited to the aforementioned problems, and other problems that are not mentioned may be clearly understood by those skilled in the art from the following description.

Technical Solution

To achieve the object, the present invention provides a stem cell proliferation method, the method including:

i) culturing cells;

ii) preparing a hydrogel-free 3D cell culture plate for producing stem cells;

iii) reprogramming the cultured cells into stem cells in the hydrogel-free 3D cell culture plate;

iv) forming a spheroid of the reprogrammed stem cells;

v) preparing a hydrogel-free 3D cell culture plate for subculturing; and vi) subculturing the spheroid in the hydrogel-free 3D cell culture plate once or more by separating the spheroid, wherein the 3D cell culture plate includes:

a well plate including a plurality of main wells and a plurality of sub wells formed at lower portions of the main wells to be injected with a cell culture solution and including recessed parts on a bottom surface thereof; and a connector for large-capacity and high-speed high content screening (HCS), which supports the well plate, and the connector for high content screening (HCS) includes a base equipped with a fixing means so as to be attached to and detached from a lower end of the well plate and a cover positioned on an upper portion of the well plate to be coupled to the base, the main well has a step formed so as to be tapered at a predetermined site, and the step has an inclination angle (9) ranging from 10 to 60° with respect to a wall of the main well.

The cells may be somatic cells or stem cells.

The somatic cells may be fibroblasts, but are not limited thereto, and any somatic cells known in the art can be used.

The stem cells may be one or more selected from the group consisting of adult stem cells, embryonic stem cells, mesenchymal stem cells, adipose-derived stem cells, hematopoietic stem cells, cord blood stem cells, and induced pluripotent stem cells, and are not limited thereto, and any can be used as long as the stem cells are known in the art.

The cells may be cultured in a general 2D well plate, a 3D cell culture plate, or a 3D plate according to the present invention.

The hydrogel may be an extracellular matrix-based hydrogel.

The extracellular matrix-based hydrogel may be Matrigel (product name).

The subculturing may be subculturing for 1 to 20 generations, but is not limited thereto.

In step vi), the spheroid may be separated into single cells and the single cells are subcultured once or more.

The sub well of the 3D cell culture plate may have an inclined surface formed so as to taper toward the recessed part, the sub wells may have an upper end diameter ranging from 3.0 to 4.5 mm, the recessed parts may have an upper end diameter ranging from 0.45 to 1.5 mm, an inclined surface ($\theta_2$) between the sub well and the recessed part may range from 40 to 50°, and a length ratio of the diameter of the sub wells to the diameter of the recessed parts may range from 1:0.1 to 0.5.

The main wells of the 3D cell culture plate may have an individual volume ranging from 100 to 300 μl, the recessed parts may have an individual volume ranging from 20 to 50 μl, and an individual volume ratio of the main well to the recessed part may be 1:0.1 to 0.5 on average.

The main well includes a space part between the step and the sub well, the space part may have a height ($a_h$) ranging from 2.0 to 3.0 mm on average, the sub well may have a height ($b_h$) from 1.0 to 2.0 mm on average, and a height ratio ($a_h$:$b_h$) of the space part to the sub well may range from 1:0.3 to 1.

The somatic cells may be seeded in the sub wells of the cell culture plate at 100 to 1000 cells/well.

The present invention provides a well plate comprising: well structures having a repeating pattern, each of the well structures is continuously provided with a space part in between a main well to be injected with a cell culture solution and a sub well including a recessed part where cells are cultured, wherein the main well is connected to the space part with forming a step, and the sub well is connected to the space part with forming a inclined surface.

The step may have an inclination angle (θ1) has ranging from 10 to 60° with respect to a wall of the main well.

The inclined surface may have an inclination angle (θ2) ranging from 30 to 80° with respect to a wall of the space part.

The recessed part may be provided in contact with the inclined surface.

The sub well may have an upper end diameter ranging from 3.0 to 4.5 mm.

The recessed part may have an upper end diameter ranging from 0.45 to 1.5 mm.

A length ratio of the upper end diameter of the sub wells to the upper end diameter of the recessed parts may range from 1:0.1 to 0.5.

The main well may have an individual volume ranging from 100 to 300 μl.

The recessed part may have an individual volume ranging from 20 to 50 μl.

An individual volume ratio of the main well to the recessed part may be 1:0.1 to 0.5.

The space part may have a height ($a_h$) ranging from 2.0 to 3.0 mm.

The sub well may have a height ($b_h$) ranging from 1.0 to 2.0 mm.

A height ratio ($a_h$:$b_h$) of the space part to the sub well may range from 1:0.3 to 1.

The present invention provides a 3D cell culture plate comprising:

aforementioned the well plate; and a connector for large-capacity and high-speed high content screening (HCS) which supports the well plate, wherein the connector for high content screening (HCS) comprises a base equipped with a fixing means so as to be attached to and detached from a lower end of the well plate, and a cover positioned on an upper portion of the well plate to be coupled to the base.

Hereinafter, the present invention will be described in detail.

Since the present invention may be modified in various forms and include various exemplary embodiments, specific exemplary embodiments will be illustrated in the drawings and described in detail in the Detailed Description.

However, the description is not intended to limit the present invention to the specific embodiments, and it is to be understood that all the changes, equivalents and substitutions included in the idea and technical scope of the present invention are included in the present invention. When it is determined that the detailed description of the related publicly known art in describing the present invention may obscure the gist of the present invention, the detailed description thereof will be omitted.

The terms used in the present application are used only to describe specific embodiments, and are not intended to limit the present invention. Singular expressions include plural expressions unless the context clearly indicates otherwise.

In the present invention, the term "include" or "have" is intended to indicate the presence of the characteristic, number, step, operation, constituent element, part or any combination thereof described in the specification, and should be understood that the presence or addition possibility of one or more other characteristics or numbers, steps, operations, constituent elements, parts or any combination thereof is not pre-excluded.

In general, when cells, spheroids, organoids, and the like are cultured, a hydrogel is used to provide the role of an extracellular matrix. In general, when induced pluripotent stem cells are reprogrammed using a 2D plate or a 3D cell culture plate, the cell culture plate is coated with an extracellular matrix-based hydrogel (for example, Matrigel) and used.

However, the present invention provides a method of producing induced pluripotent stem cells using a 3D cell culture plate which does not include a hydrogel. A specific description on the 3D cell culture plate of the present invention is as follows.

In an exemplary embodiment, the present invention uses a 3D cell culture plate including:

a well plate including a plurality of main wells and a plurality of sub wells formed at lower portions of the main wells to be injected with a cell culture solution and including recessed parts on a bottom surface thereof; and a connector for large-capacity and high-speed high content screening (HCS), which supports the well plate, wherein the connector for high content screening (HCS) includes a base equipped with a fixing means so as to be attached to and detached from a lower end of the well plate and a cover positioned on an upper portion of the well plate to be coupled to the base, the main well has a step formed so as to be tapered at a predetermined site, and the step has an inclination angle ($\theta$) ranging from 10 to 60° with respect to a wall of the main well.

A 96-well plate in the related art has a problem in that it takes a lot of time and costs because experiments and analyses should be performed several times or more in order to evaluate the efficacy of a drug in high yield. Furthermore, there is a case where the pipetting work of replacing a culture solution during cell culture is often performed, and in the case of a Corning spheroid microplate in the related art, spheroids or organoids in cell culture are affected, so that there was a problem which is not good for the cell culture environment because there is a case where spheroids or organoids are sucked up or the positions thereof are changed during the pipetting work.

Therefore, the present invention has been made in an effort to solve the above-described problems, and provides a cell culture plate capable of manufacturing spheroids/organoids in high yield by including a plurality of sub wells in a plurality of main wells in a well plate, and capable of uniformly capturing images in the well plate by including a connector for large-capacity high-speed high content screening (HCS), which supports the well plate to reduce a tolerance when a large-capacity and high-speed image is captured. Furthermore, the present invention provides a cell culture plate capable of minimizing the effects of the pipetting work during replacement of a medium on cells to be cultured by the step of the main well.

Hereinafter, preferred exemplary embodiments of the present invention will be described in detail with reference to the accompanying drawings. Prior to the description, terms or words used in the specification and the claims should not be interpreted as being limited to a general or dictionary meaning and should be interpreted as a meaning and a concept which conform to the technical spirit of the present invention based on a principle that an inventor can appropriately define a concept of a term in order to describe his/her own invention by the best method.

Accordingly, since the exemplary embodiments described in the present specification and the configurations illustrated in the drawings are only the most preferred exemplary embodiments of the present invention and do not represent all of the technical spirit of the present invention, it is to be understood that various equivalents and modified examples, which may replace the exemplary embodiments and the configurations, are possible at the time of filing the present application.

FIG. 1A is a front view of a cell culture plate according to an exemplary embodiment of the present invention, FIG. 1B is a cross-sectional view of the cell culture plate according to an exemplary embodiment of the present invention, FIG. 2 is a view illustrating a main well formed in the cell culture plate according to an exemplary embodiment of the present invention, and FIG. 3 is a view illustrating a well plate, a base and a cover of the cell culture plate according to an exemplary embodiment of the present invention ((A) a cover, (B) a base, and (C) a fixing means of a microplate and a base).

Hereinafter, a cell culture plate according to an exemplary embodiment of the present invention will be described in detail with reference to FIGS. 1 to 3.

As illustrated in FIGS. 1 to 3, a cell culture plate 10 according to an exemplary embodiment of the present invention includes a well plate 100 including a plurality of main wells 110 and a plurality of sub wells 120 formed at lower portions of the main wells 110 to be injected with a cell culture solution and including recessed parts 121 on a bottom surface thereof; and a connector 200 for large-capacity and high-speed high content screening (HCS), which supports the well plate 100.

First, the well plate 100 according to an exemplary embodiment of the present invention will be described in detail.

The well plate 100 is made into a plate shape that is plastic injection-molded through a mold. In order to manufacture a mold for plastic injection as described above, the main well 110 has a repeating pattern as a well structure such that the unit cost of production can be reduced and the size can be easily increased using fine machining. Therefore, cells are easily mass-produced, and the cells can be transformed into various sizes according to the user's requirements and used.

A plurality of the main wells 110 is formed in the well plate 100, and each main well 110 includes a step 101. The step 101 is formed at a predetermined site of the main well 110, and more specifically, the step 101 may be formed at a position which is 1/3 to 1/2 of a total length of the main well 110, and the step 101 may be formed at a position which is 1/3 to 1/2 of the total length from the lower end of the main well 110.

In the related art, there is a case where the pipetting work of replacing a culture solution during cell culture is performed, and in this case, spheroids or organoids in cell culture are affected, so that there is a problem which is not good for the cell culture because there is a case where the spheroids or organoids are sucked up or the positions thereof are changed during the pipetting work, but the step 101 is provided to prevent this problem.

The step 101 may be a space to which a pipette is applied, and specifically, may have an inclination angle ($\theta$) ranging from 10 to 60° with respect to a wall of the main well 110. Alternatively, the step 101 may have an inclination angle ranging from 20 to 50°, preferably ranging from 30 to 45°.

When the inclination angle of the step 101 is less than 10°, the inclination angle within the main well 110 is so small that the space to which a pipette can be applied is not sufficient, and as a result, when the culture solution in the main well 110 is sucked up, the pipette may slide inside the sub well 120, causing spheroids or organoids to be sucked up, or the positions thereof, and the like to be changed. Furthermore, when the inclination angle (θ) exceeds 60°, a space to which a pipette can be applied is provided, but the inclination angle of the step 101 is so large that it may be difficult to sufficiently suck up the culture solution, and when cells are seeded on the sub well 120, a problem in that cells are seeded on the step 101 without entering all the sub wells 120 may occur. Therefore, it is desirable to have an inclination angle in the above-described range.

Meanwhile, the main well according to an exemplary embodiment of the present invention may include a space part 130 between the step 101 and a sub well 120 to be described below. Specifically, the space part 130 is a space into which a culture solution is injected, and is a space in which cells inside the sub well 120 can share the same culture solution.

More specifically, the space part 130 may have a height ($a_h$) ranging from 2.0 to 3.0 mm on average, or ranging from 2.2 to 2.8 mm, or ranging from 2.3 to 2.7 mm on average. Furthermore, the sub well 120 may have a height ($b_h$) ranging from 1.0 to 2.0 mm on average, or ranging from 1.2 to 1.8 mm on average.

For example, the space part 130 may have a height ($a_h$) of 2.5 mm on average, and the sub well may have a height ($b_h$) of 1.5 mm on average.

In this case, a height ratio ($a_h:b_h$) of the space part to the sub well may range from 1:0.3 to 1, and more specifically, a height ratio ($a_h:b_h$) of the space part to the sub well 120 may be 1:0.4 to 0.9 or 1:0.5 to 0.8. When a ratio of the height of the sub well 120 to the height of the space part is less than 1:0.3, the cells in culture may escape from the inside even with a small force during the exchange of the media of the sub well 120, and when a ratio of the height of the sub well 120 to the height of the space part exceeds 1:1, the culture solution required for the cells is not sufficiently converted, so that cell death may be induced. Therefore, it is preferred that the space part 130 and the sub well 120 have the above-described height range and height ratio.

Next, the sub wells 120 are formed at lower portion of each of the main wells 110 and include recessed parts 121 on a bottom surface thereof. As a particular aspect, the sub well 120 may include a plurality of recessed parts at lower portions of the main well 110.

The sub wells 120 included at the lower portion of the main well 110 have the same size and shape, thereby enabling spheroids and organoids to be produced under uniform conditions.

The sub well 120 may have an inclined surface formed so as to taper toward the recessed part 121. Specifically, the horizontal area of the upper portion of the sub well 120 may become smaller as it descends in the vertical direction. For example, the upper portion of the sub well 120 may be formed in an inverted pyramid shape. In the illustrated exemplary embodiment, the upper portion of the sub well 120 may be formed in a shape such as a pyramid shape or a funnel shape in which the horizontal area of the upper portion of the sub well 120 becomes smaller as it descends in the vertical direction.

In particular, the cell culture plate may produce a large amount of spheroids or organoids under uniform conditions by including a plurality of the sub wells 120 so as to have the same size and shape.

As a particular aspect, one main well 110 can include 4 to 25 sub wells 120 of the same size, and the entire microplate 100 may include 96 to 1,728 sub wells 120. Accordingly, the size can be controlled in the same precise manner.

Furthermore, the sub well 120 includes a recessed part 121, and a space is formed in the lower portion of the recessed part such that 3D spheroids or an organoids can be cultured in the recessed part 121. Specifically, the recessed part 121 may be in the form of the letter 'U', 'V', or 'I{', and for example, the recessed part 121 may be in the form of the letter 'U'.

The sub well 120 may have an upper end diameter ranging from 3.0 to 4.5 mm, or ranging from 3.5 to 4.3 mm, or 4 mm on average. Furthermore, the recessed part 121 may have an upper end diameter of 0.45 to 1.5 mm, or 0.5 to 1.0 mm or 0.5 mm on average.

Furthermore, a length ratio of the diameter of the sub well 120 to the diameter of the recessed part 121 may range from 1:0.1 to 0.5, and preferably, a length ratio of the diameter of the sub well 120 to the diameter of the recessed part 121 may be 1:0.12.

When the upper end diameter of the recessed part 121 is less than 0.1 compared to the upper end diameter 1 of the sub well 120, a cell culture space of the recessed part 121 cannot be sufficiently provided, which may cause a problem in that cells escape even with a small force during the replacement of the culture solution, and when the upper end diameter of the recessed part 121 is exceeds 0.5 compared to the upper end diameter 1 of the sub well 120, a sufficient culture solution required for cells cannot be replaced, which may cause a problem in that it is difficult to stably culture cells.

Meanwhile, an inclination surface between the sub well 120 and the recessed part 121 may have an inclination angle ($θ_2$) of 30 to 80°, 40 to 50°, 42 to 48°, 43 to 47°, or an inclination angle ($θ_2$) of 450 on average, with respect to a wall of the main well.

The above-described sub well 120 has an advantage in that cells can be cultured at 100 to 1000 cells/well or less, and the spheroid size can be stably controlled.

Further, the main well 110 according to an exemplary embodiment of the present invention has an individual volume ranging from 100 to 300 μl, the recessed part 121 has an individual volume ranging from 20 to 50 μl, and an individual volume ratio of the main well 110 to the recessed part 121 is characterized by being 1:0.07 to 0.5 on average. Preferably, the main well according to an exemplary embodiment has an individual volume ranging from 250 to 300 μl, the recessed part has an individual volume ranging from 25 to 35 μl, and an individual volume ratio of the main well 110 to the recessed part 121 may be 1:0.11 on average.

Specifically, when the main well 110 has an individual volume less than 100 μl, a problem in that a sufficient culture solution cannot be accommodated during cell culture may occur, and when the individual volume exceeds 300 μl, culture efficiency may be reduced.

Furthermore, the recessed part 121 is a space in which cells are substantially cultured, and when the volume is less than 20 μl, the cell culture space is not sufficient, which may cause a problem in that cells escape, and when the volume exceeds 50 μl, a problem in that it is difficult to stably culture cells and the like may occur. Therefore, it is preferred that the main well 110 and the recessed part 121 have volumes in the above-described ranges.

Due to the above-mentioned configuration of the cell culture plate of the present invention, reprogramming into induced pluripotent stem cells occurs at high efficiency without including a hydrogel, that is, without coating the cell culture plate with a hydrogel, and the spheroid is also formed well after the reprogramming.

Further, when the spheroid is separated and subcultured in the cell culture plate of the present invention, the spheroid is formed very well. Specifically, hundreds to thousands of monoclonal induced pluripotent stem cells may be produced by separating the spheroid into single cells and subculturing the single cells.

The cell culture plate 10 according to an exemplary embodiment of the present invention includes a connector 200 for large-capacity and high-speed high content screening (HCS), which supports the well plate 100. Herein, the connector 200 for large-capacity and high-speed high content screening (HCS) refers to a connector 200 which is attached to a high content screening (HCS) system, and specifically, the connector may refer to a base 210 and a cover 220 in the present invention.

More specifically, the connector for large-capacity and high-speed high content screening (HCS) includes the base 210 equipped with fixing means 140 and 240 so as to be attached to and detached from a lower end of the well plate 100 and a cover 220 positioned on an upper portion of the well plate 100 to be coupled to the base 210. Moreover, the upper end of the base 210 and the lower end of the well plate 100 are characterized by including fixing means 140 and 240 that can be fixed so as to be attached to and detached from each other.

In this case, the base includes a convex part 240 for supporting the well plate 100, and the well plate 100 may include a concave part 140 facing the convex part 240 of the base 210. The well plate 100 may be fixed by the fixing means to uniformly capture images during screening.

The base may be formed of a polyethylene, polypropylene, polystyrene, polyethylene terephthalate, polyamide, polyester, polyvinyl chloride, polyurethane, polycarbonate, polyvinylidene chloride, polytetrafluoroethylene, polyether ether ketone or polyetherimide material, but is not limited thereto.

The well plate may be formed of a polydimethylsilicone, high-fat modified silicone, methylchlorophenyl silicone, alkyl-modified silicone, methylphenylsilicone, silicone polyester, or amino-modified silicone material, but is not limited thereto.

Meanwhile, when induced pluripotent stem cells are formed in the cell culture plate 10 of the present invention, Matrigel need not be used.

FIG. 4 illustrates a comparison of a method of producing induced pluripotent stem cells using a 2D cell culture plate that uses Matrigel and a method of producing induced pluripotent stem cells using a 3D cell culture plate that does not require Matrigel according to the present invention. After somatic cells (fibroblasts) are cultured, induced pluripotent stem cells are produced by transfecting the fibroblasts with an episomal vector by electroporation to induce reprogramming. In the case of 2D Matrigel culture, the process of collecting a colony of induced pluripotent stem cells is complicated, and the yield is low. However, when the 3D culture plate of the present invention is used, there is no Matrigel, so that a number of single cells reprogrammed into induced pluripotent stem cells gather to form a spheroid, which is a 3D spherical cell aggregate. This spheroid can be easily separated from a 3D cell culture plate, and can be sub-cultured (FIG. 7D). That is, reprogramming efficiency is very high.

Further, as previously described, for the 3D cell culture plate used in the present invention, one main well 110 can include 4 to 25 sub wells 120 of the same size, and the entire microplate 100 may include 96 to 1,728 sub wells 120. Accordingly, it is possible to mass-produce induced pluripotent stem cells and spheroids thereof whose sizes can be controlled in the same precise manner.

FIG. 10 schematically illustrates the method of mass proliferating induced pluripotent stem cell spheroids obtained in the step of reprogramming induced pluripotent stem cells. It can be seen that compared to the 2D cell culture plate (coated with Matrigel), the induced pluripotent stem cell proliferation rate of the present invention is very high. In addition, when spheroids are separated into single cells and the single cells are plated again, and then subcultured, hundreds to thousands of uniformly sized monoclonal spheroids are produced, so that an induced pluripotent stem cell spheroid bank may also be produced.

Advantageous Effects

According to the production method of the present invention, it is possible to mass-proliferate stem cells with enhanced reprogramming efficiency without the need for a hydrogel. Further, a monoclonal stem cell spheroid bank can be produced.

DESCRIPTION OF DRAWINGS

FIG. 3A is a view illustrating a cover of the cell culture plate according to an exemplary embodiment of the present invention.

FIG. 3B is a view illustrating a base of the cell culture plate according to an exemplary embodiment of the present invention.

FIG. 3C is a view illustrating a fixing means of a microplate and a base according to an exemplary embodiment of the present invention.

MODES OF THE INVENTION

Figure 1A:
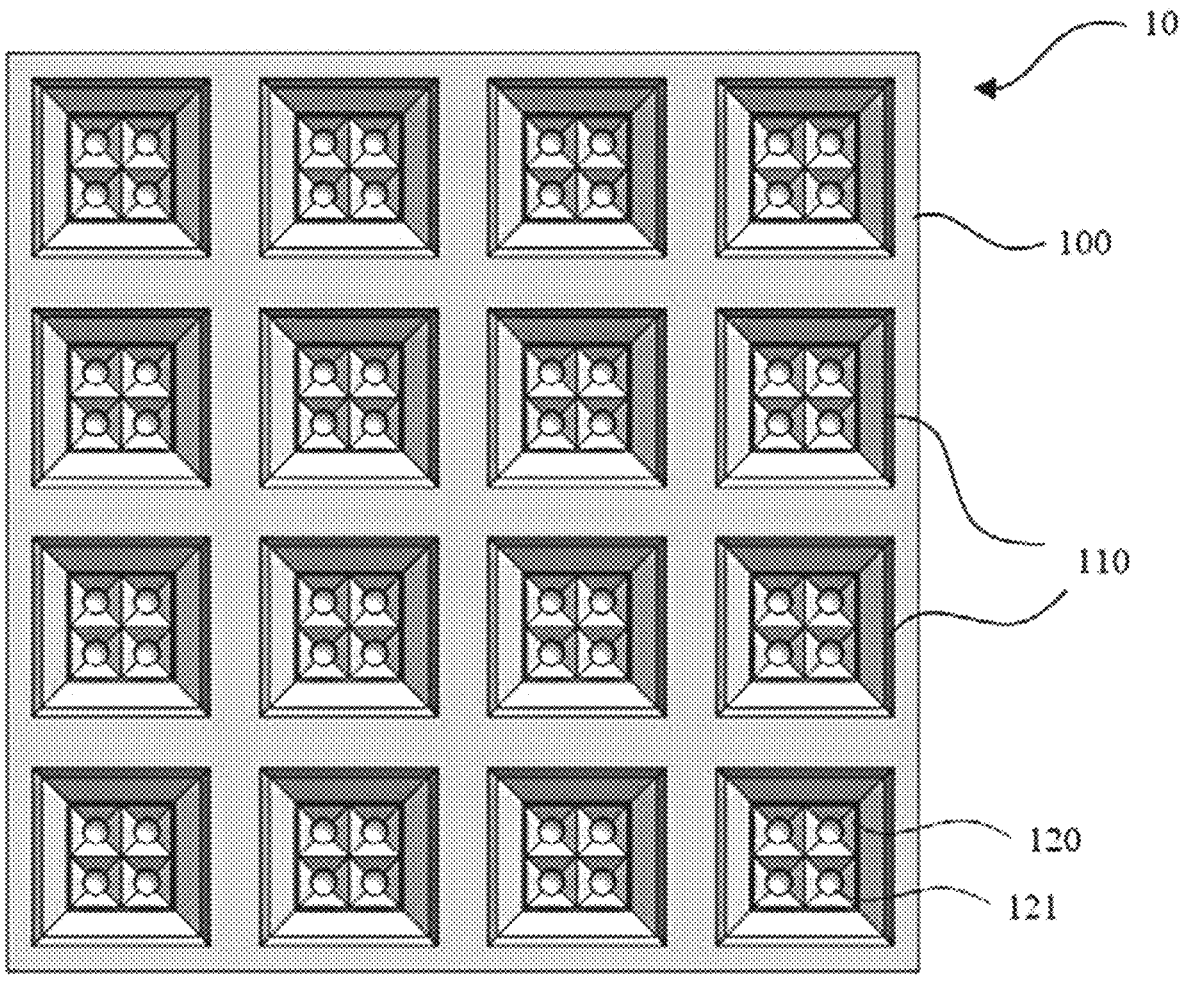
FIG. 1A is a front view of a cell culture plate according to an exemplary embodiment of the present invention.
Figure 1B:
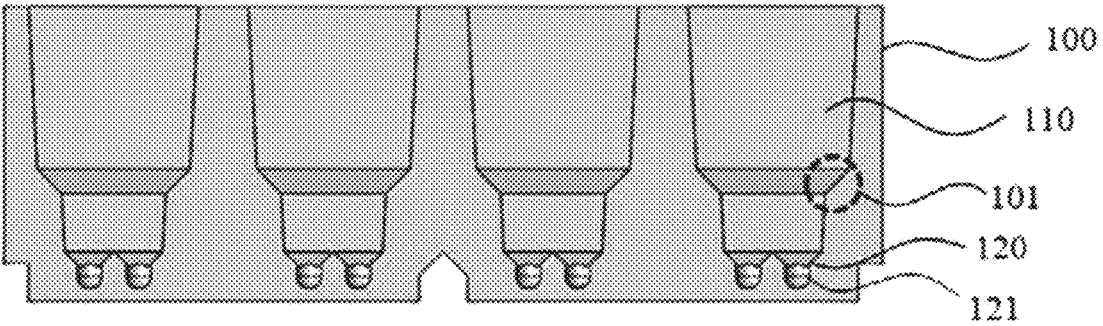
FIG. 1B is a cross-sectional view of the cell culture plate according to an exemplary embodiment of the present invention.
Figure 2:
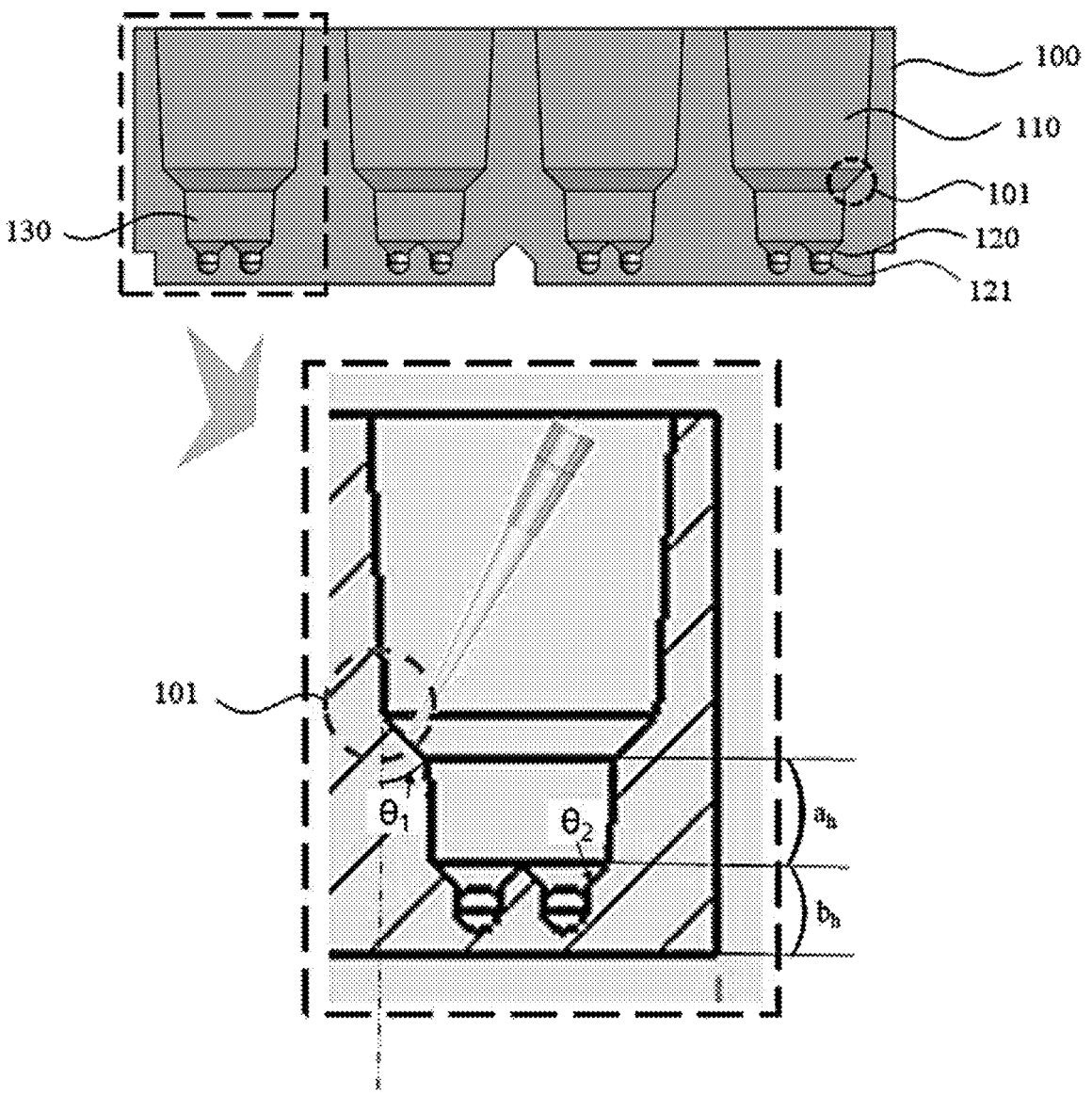
FIG. 2 is a view illustrating, in detail, a main well formed in the cell culture plate according to an exemplary embodiment of the present invention.

Since the present invention may be modified into various forms and include various exemplary embodiments, specific exemplary embodiments will be illustrated in the drawings and described in detail in the Detailed Description. However, the description is not intended to limit the present invention to the specific exemplary embodiments, and it is to be understood that all the changes, equivalents, and substitutions belonging to the spirit and technical scope of the present invention are included in the present invention. When it is determined that the detailed description of the related publicly known art in describing the present invention may obscure the gist of the present invention, the detailed description thereof will be omitted.

EXAMPLES

Example 1. Experimental Methods 1-1: Culture of Fibroblasts and Production of Induced Pluripotent Stem Cells The German federal authorities/RKI: AZ 1710-79-1-4-41 E01 (F134), which is a human fibroblast line, was cultured in a DMEM containing 10% FBS (fetal bovine serum, Invitrogen, USA) and 1 mM L-glutamine (Invitrogen, USA) in a 35 mm or 100 mm Petri dish. The cultured fibroblasts were reprogrammed by being transfected (Neon™ transfection system) with an episomal iPSC reprogramming vector (EPS™ kit: Cat. No. A16960. Invitrogen, Carlsbad, CA, USA) by electroporation. The electroporation was performed under the conditions of 1,650 V, 10 ms, and 3 pulses.

Figure 4A:
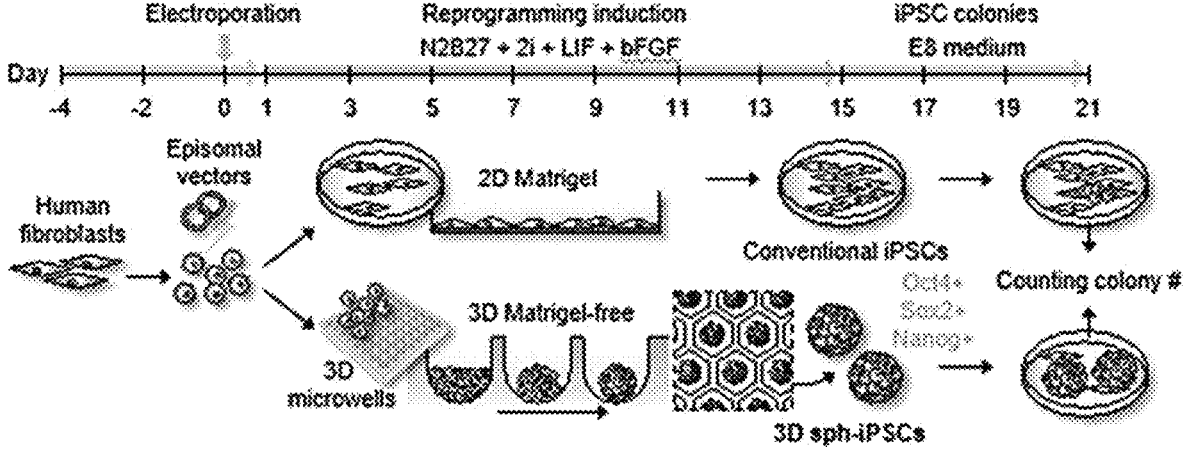
FIG. 4A schematically illustrates processes of producing induced pluripotent stem cells according to an exemplary embodiment of the present invention and a comparative example.

As illustrated in FIG. 4A, the transfected fibroblasts were inoculated in a 3D cell culture plate of the present invention (without Matrigel, the Example), a 2D 12-well plate (coated with Matrigel, Comparative Example 1) and a commercialized product Addgene (Comparative Example 2, coated with Matrigel, not illustrated in FIG. 4A), and cultured in an N2B27 medium (containing bFGF). After the fibroblasts were cultured for 15 days, the medium was replaced with an Essential 8™ medium. After 15 days, the number of colonies in the Example and the Comparative Examples were confirmed by plating 3D iPSC of the Example (3D cell culture plate) on a 12-well plate which is a 2D plate.

1-2: Reprogramming Efficiency Analysis of Fibroblasts

According to the alkaline phosphatase staining kit manual (System Biosciences, USA), reprogrammed cells were washed twice with PBS, fixed with 4% paraformaldehyde, then stained with Blue-color AP solution, washed twice with PBS, and then it was observed under an optical microscope whether the colonies were stained. The number of stained colonies was counted and quantified.

Images of the cultured cells in the Example and the Comparative Examples were captured, and the sizes of cell spheres were compared. Spheroids were subjected to imaging by an automated plate device, and in this case, the device was allowed to perform imaging by automatically focusing. Image size analysis was performed using a macro program of a program called ImageJ (related to FIGS. 5, 6 and 7).

1-3: Optimization of 3D Culture Method of Induced Pluripotent Stem Cells

Figure 8A:
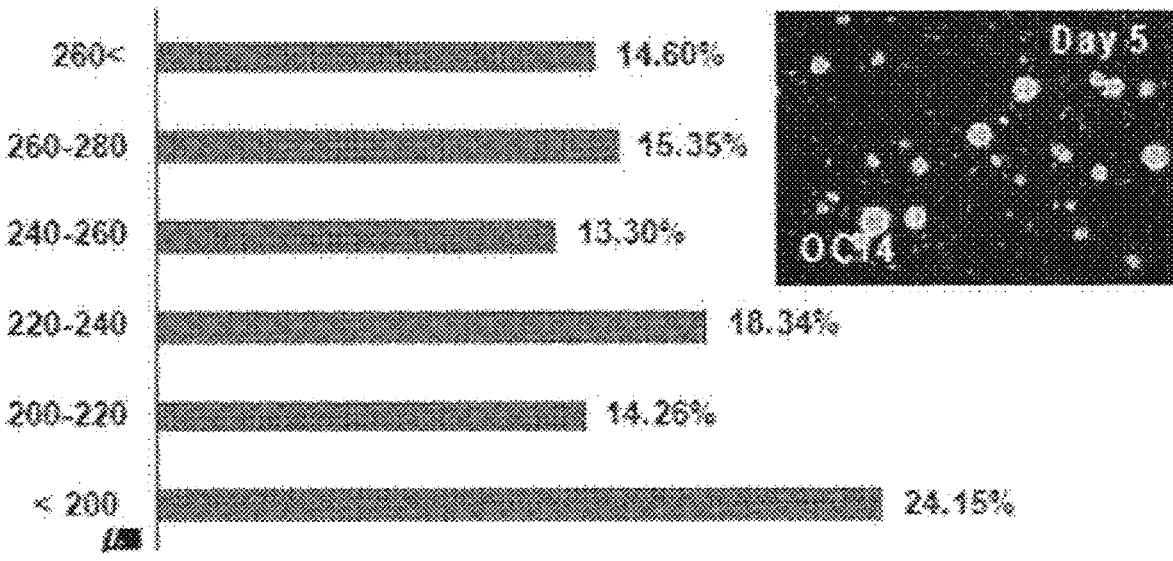
FIG. 8A is a result of showing the size distribution of spheroids (colonies) as a result of 3D culture in the related art and culture according to an exemplary embodiment of the present invention.
Figure 8A:
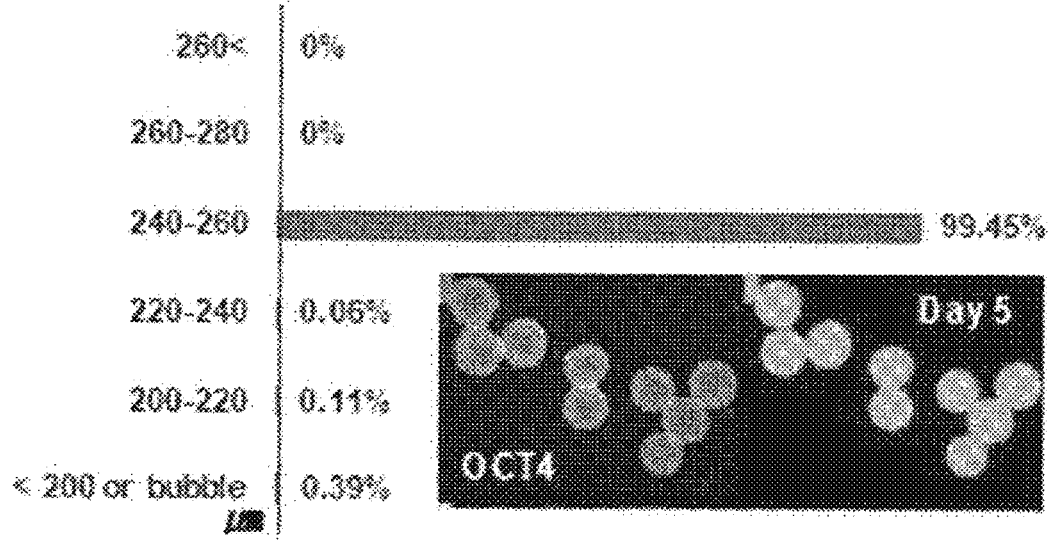

Images of the 3D induced pluripotent stem cells cultured in the Example and the Comparative Examples were captured, and accordingly, the sizes of the cell spheres were compared and measured (FIG. 8A). An external inspection company (Cell Bio CEFO, Korea) was commissioned to test the results of the images, and this test was performed as a blind test.

1-4: Immunostaining

Reprogrammed cells were fixed with 4% paraformaldehyde at room temperature for 20 minutes. After the fixed cells were reacted with PBS containing 1% BSA and 0.5% Triton X-100 at room temperature for 1 hour, the cells were treated with each of primary antibodies Oct4 (1:100, SantaCruz, CA, USA), Sox2 (1:100, Cell Signaling, Danvers, MA, USA), Nanog (1:200, Cosmo Bio, Koto-Ku, Japan), and E-cadherin (1:200, abcam), and reacted with FITC-conjugated goat anti-rabbit IgG or anti-mouse IgG (1:100, Invitrogen, Carlsbad, CA) as a secondary antibody. Fluorescent images were analyzed under a fluorescence microscope (Olympus, Shinjuku, Tokyo, Japan). DAPI was used as a nuclear staining solution.

Figure 12:
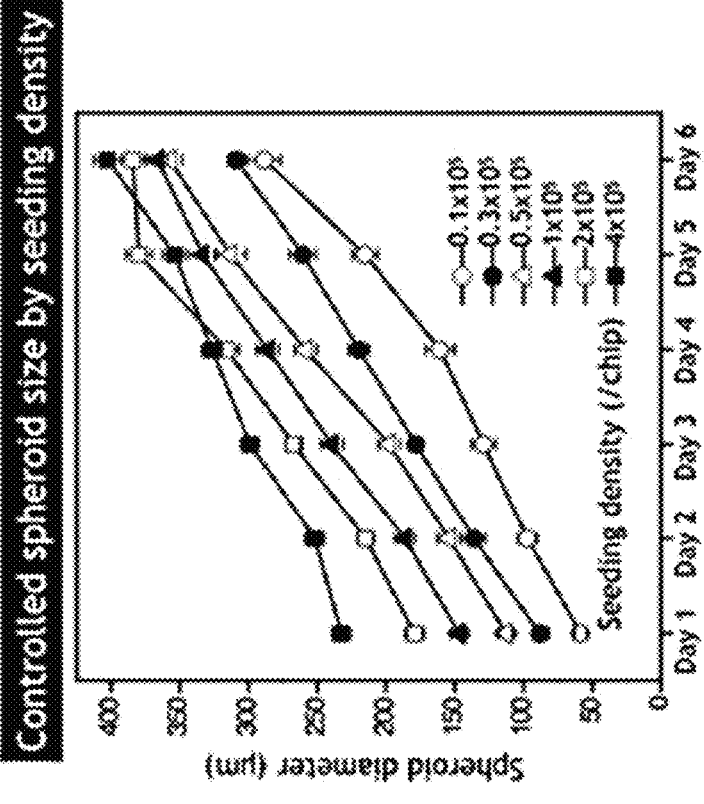
FIG. 12 is a graph showing that the size is uniformly distributed when the induced pluripotent stem cells are cultured according to an exemplary embodiment of the present invention.
Figure 12:
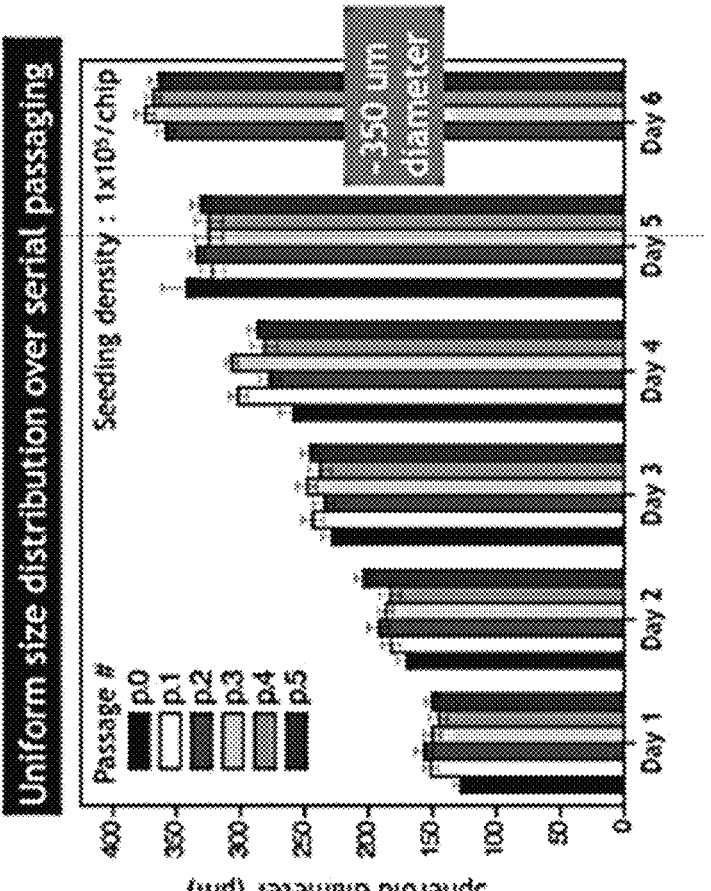

1-5: Verification of Efficiency of 3D Mass Culture of Stem Cells or Induced Pluripotent Stem Cells Induced pluripotent stem cells were seeded with different numbers of cells, and size comparisons were performed by date. It was verified that by putting 0.1, 0.3, 0.5, 1, 2, $4\times10^5$ cells, respectively, into the multi-well corresponding to the example, the cell size was maintained and the cell number is constantly increased regardless of the number of cells (related to FIGS. 12 and 13).

As a result of comparing the increases in these cell numbers, it was confirmed that as a result of comparing the numbers of 2D cultured cells at the same period, the number of cells was increased by 22.9±4.33%.

1-6: qPCR

Total RNA was extracted from fibroblasts and reprogrammed cells using an RNA minikit (Qiagen, Inc.), and then converted to cDNA using the Accupower RT mix reagent (Bioneer Corp., Seoul, Korea). qPCR was performed using Real-time PCR FastStart Essential DNA Green Master Mix (Roche, Indianapolis, IN, USA). The primer sequences used in the present invention are as follows in Table 1.

TABLE 1

| Genes | | Primer sequences (5'-3') |
|---|---|---|
| hCOL1A1 | forward | ATGACTATGAGTATGGGGAAGCA |
| | reverse | TGGGTCCCTCTGTTACACTTT |
| hOCT4 | forward | AATTTGTTCCTGCAGTGCCC |
| | reverse | AGACCCAGCAGCCTCAAAAT |
| hNANOG | forward | GGATCCAGCTTGTCCCCAAA |
| | reverse | TGCGACACTCTTCTCTGCAG |
| hSOX2 | forward | CGGAAAACCAAGACGCTCAT |
| | reverse | GTTCATGTGCGCGTAACTGT |
| hLIN28 | forward | TTCGGCTTCCTGTCCATGAC |
| | reverse | CCGCCTCTCACTCCCAATAC |

Example 2. Confirmation of Reprogramming Efficiency

Figure 4B:
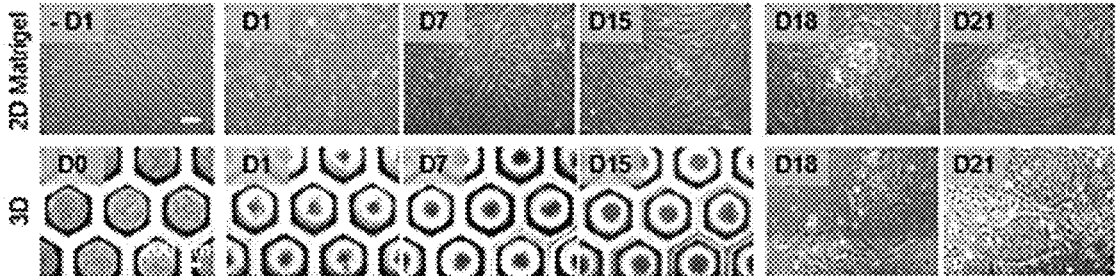
FIG. 4B is a set of images illustrating the generation of induced pluripotent stem cells according to an exemplary embodiment of the present invention and a comparative example (In all of the drawings below FIG. 4, for the convenience of description, the 3D cell culture plate of the present invention is not accurately displayed, but is displayed in a U shape for convenience.)
Figure 5:
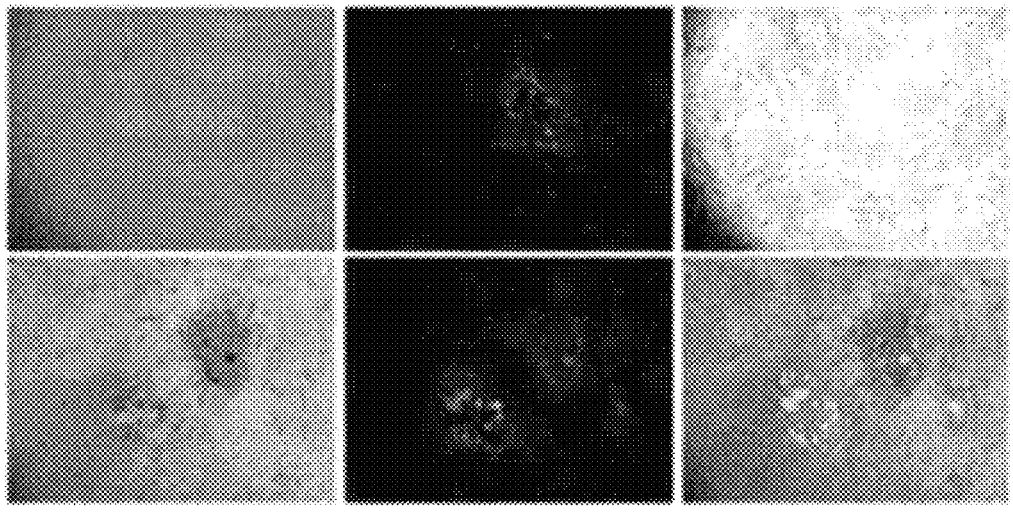
FIG. 5 is a set of images of an exemplary embodiment (3D iPSC) of the present invention and a comparative example (2D iPSC).
Figure 5:
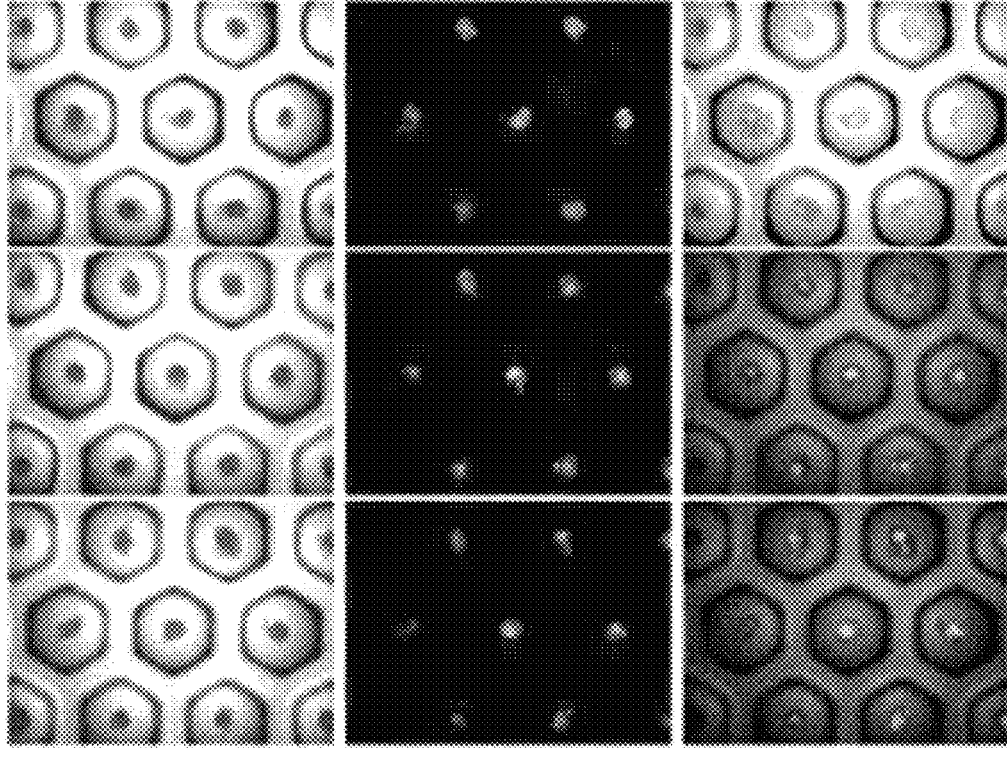
Figure 6:
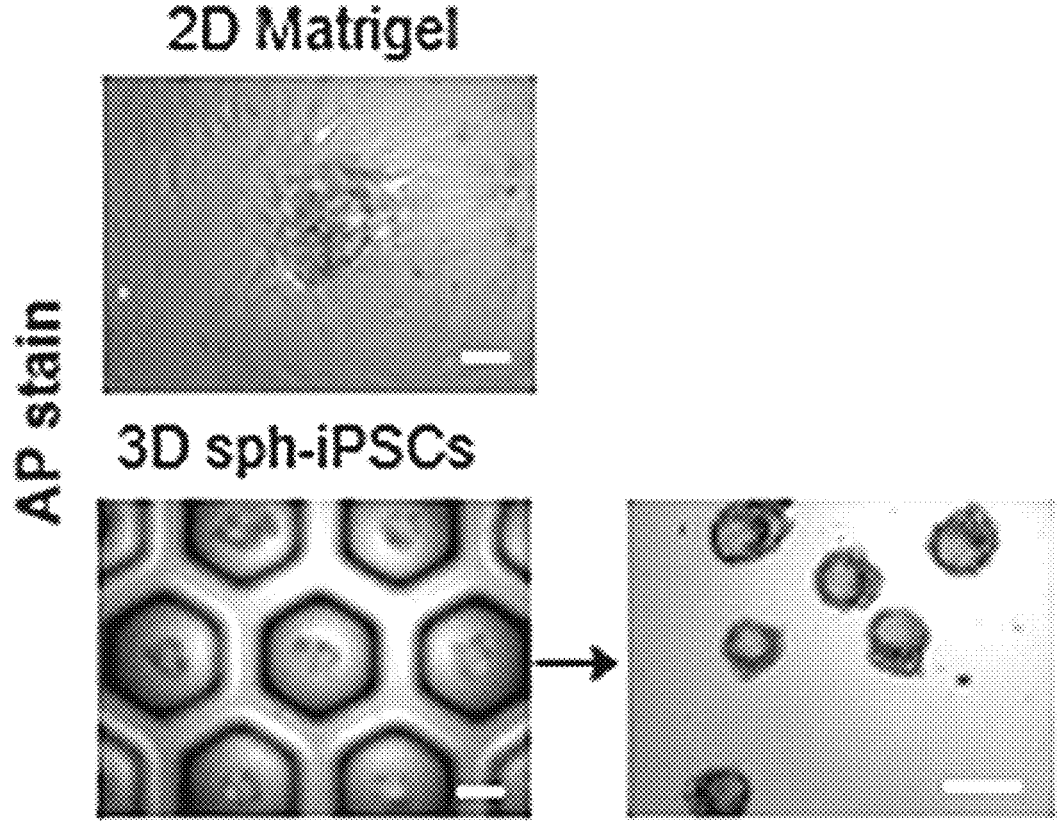
FIG. 6 is an alkaline phosphatase (AP) stained image of an exemplary embodiment (3D sph-iPSC) of the present invention and a comparative example (2D Matrigel).
Figure 7A:
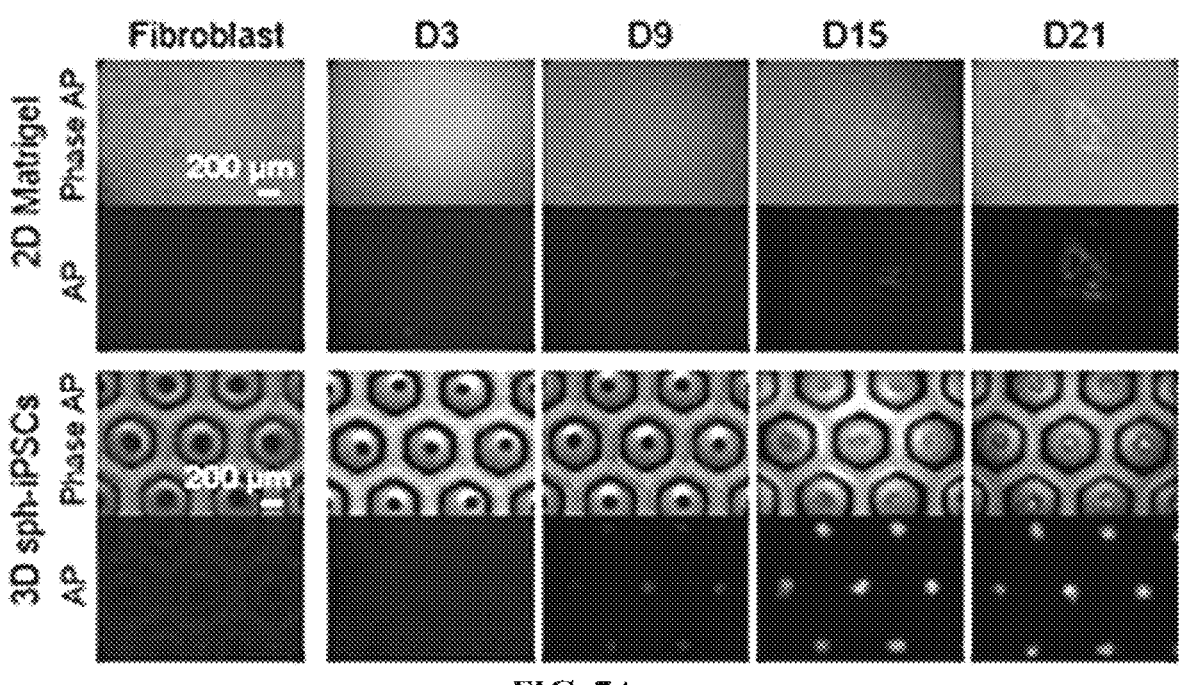
FIG. 7A is an AP image (D4, D9, D15, D21) over time, FIG. 7B compares the number of colonies.
Figure 7B:
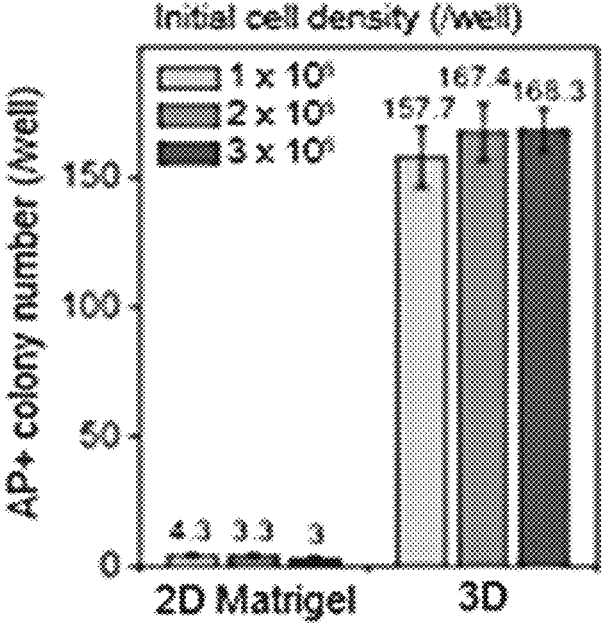
FIG. 7C is an E-cadherin expression result.
FIG. 7D illustrates the process of forming a spheroid of iPSCs.

Referring to FIG. 4B, it can be seen that in the case of 2D culture, a small amount of colonies begin to be formed only at D15. After iPSC reprogramming was induced up to D15, 3D iPSCs were plated on a 2D plate, and the number of colonies in Comparative Example 1 and Example 1 was compared by plating 3D iPSCs on a 2D plate, and as a result, the difference in the number of colonies formed was large. It can be seen that the iPSC reprogramming yield of the Example is high because the cells that are well differentiated into iPSCs forming a colony. Referring to FIGS. 5 and 7B, it can be seen that the difference in the number of colonies is very large between the 2D culture (Comparative Example 1) and the 3D culture (the Example). Referring to FIG. 6, it can be seen that as a result of alkaline phosphatase (AP) staining, the reprogramming efficiency is very high in 3D iPSC spheroids (the Example, 3D sph-iPCSs). Further, referring to FIGS. 6 and 7A, when 2D Matrigel (Comparative Example 1) and 3D iPSC spheroids (the Example, 3D sph-iPCSs) are compared with each other, the images appear uniform and clear, showing that the 3D cell culture plate of the present invention is capable of large-scale image analysis.

Figure 7C:
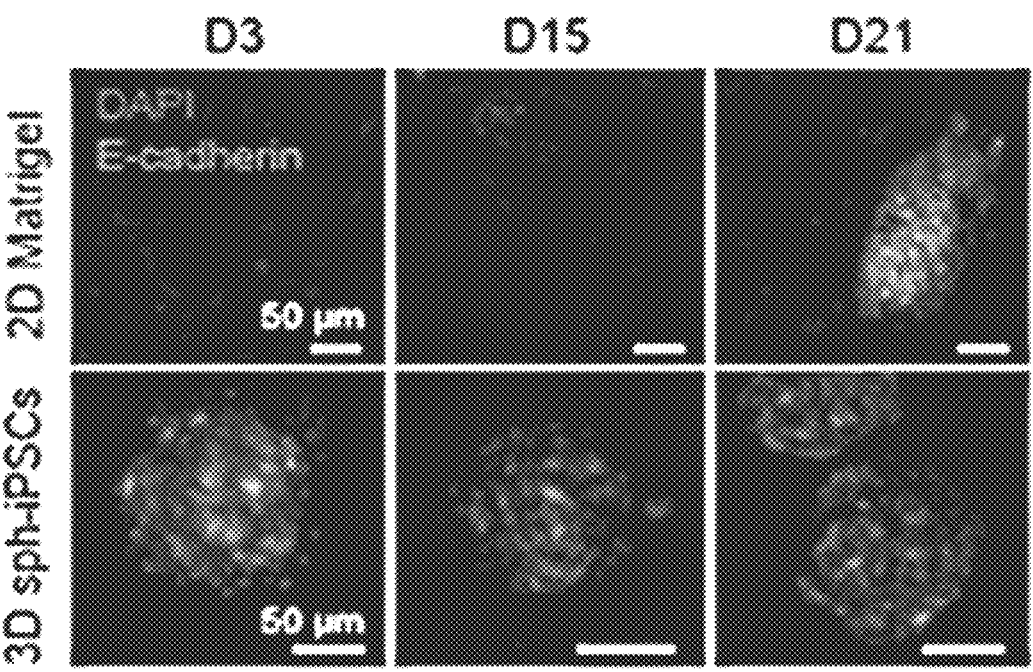
Figure 7D:
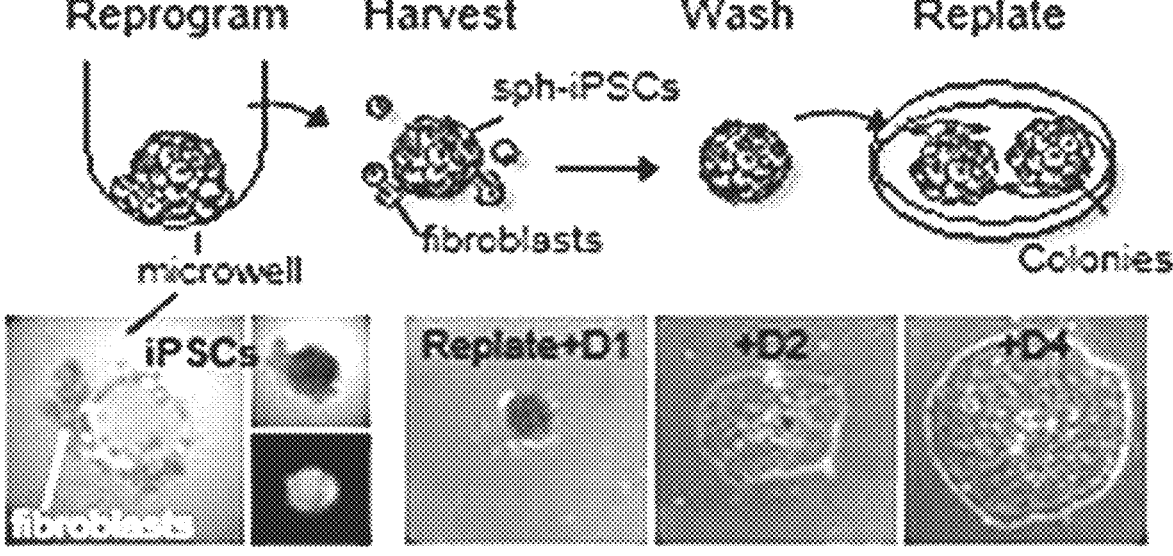

Referring to FIG. 7C, it can be seen that the reprogramming efficiency in the 3D cell culture plate is very good. In addition, referring to FIG. 7D, it can be seen that since the present invention does not use Matrigel, a large number of single cells reprogrammed into iPCSs gather to form a spheroid, which is a spherical cell aggregate, and these spheroids can be easily separated from the 3D cell culture plate and re-plated. That is, reprogramming efficiency is very high.

Figure 8B:
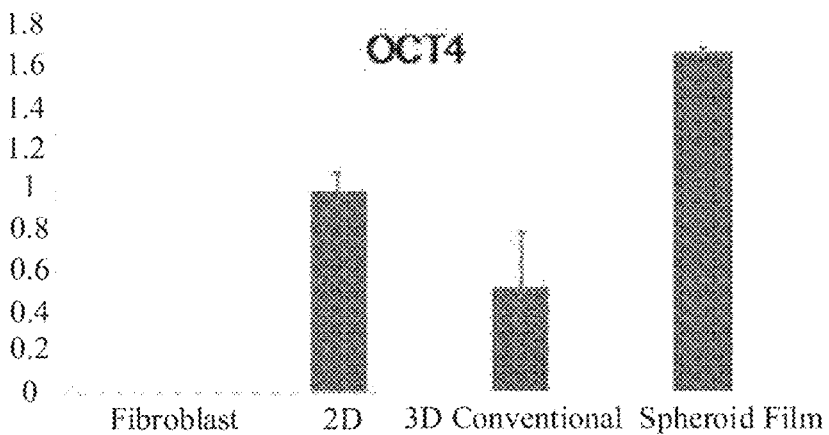
FIG. 8B is the expression result of a reprogramming factor (pluripotency marker).
Figure 8B:
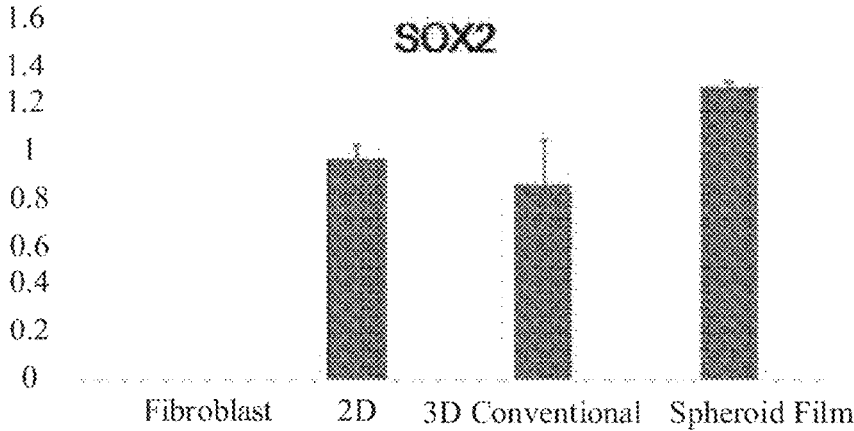
Figure 8B:
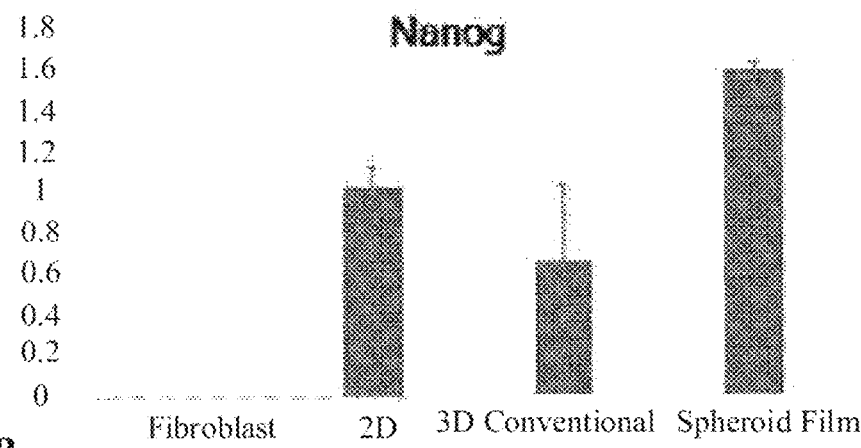

FIG. 8 compares the 3D culture in the related art of Comparative Example 2 with the 3D culture of the Example of the present invention (SpheroidFilm in FIG. 8B). The 3D culture in the related art is not uniform in size and has a relatively low expression level of oct4. However, the present invention is very uniform in size (99.45%) and has a very high reprogramming factor expression level. That is, the present invention is effective in stem cell culture even when compared to the 3D culture in the related art, and can increase the efficiency of reprogramming somatic cells into induced pluripotent stem cells. Furthermore, a uniform size means that standardized induced pluripotent stem cells and stem cells can be three-dimensionally mass-produced in the form of a spheroid.

Example 3. Analysis of Characteristics of Stem Cells

Figure 9A:
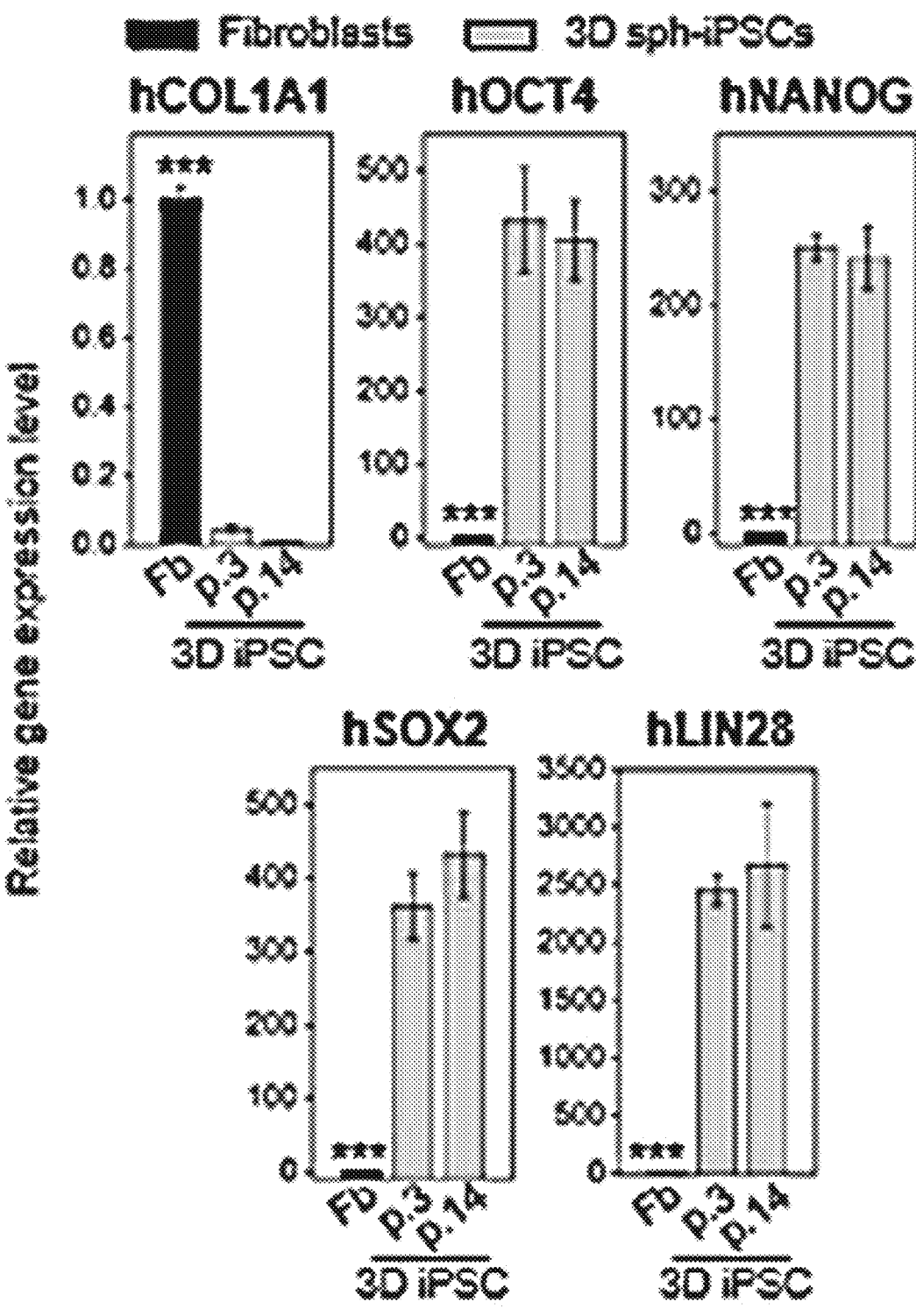
FIGS. 9A and 9B illustrate the expression results of pluripotency markers of iPSCs according to an exemplary embodiment of the present invention.
Figure 9B:
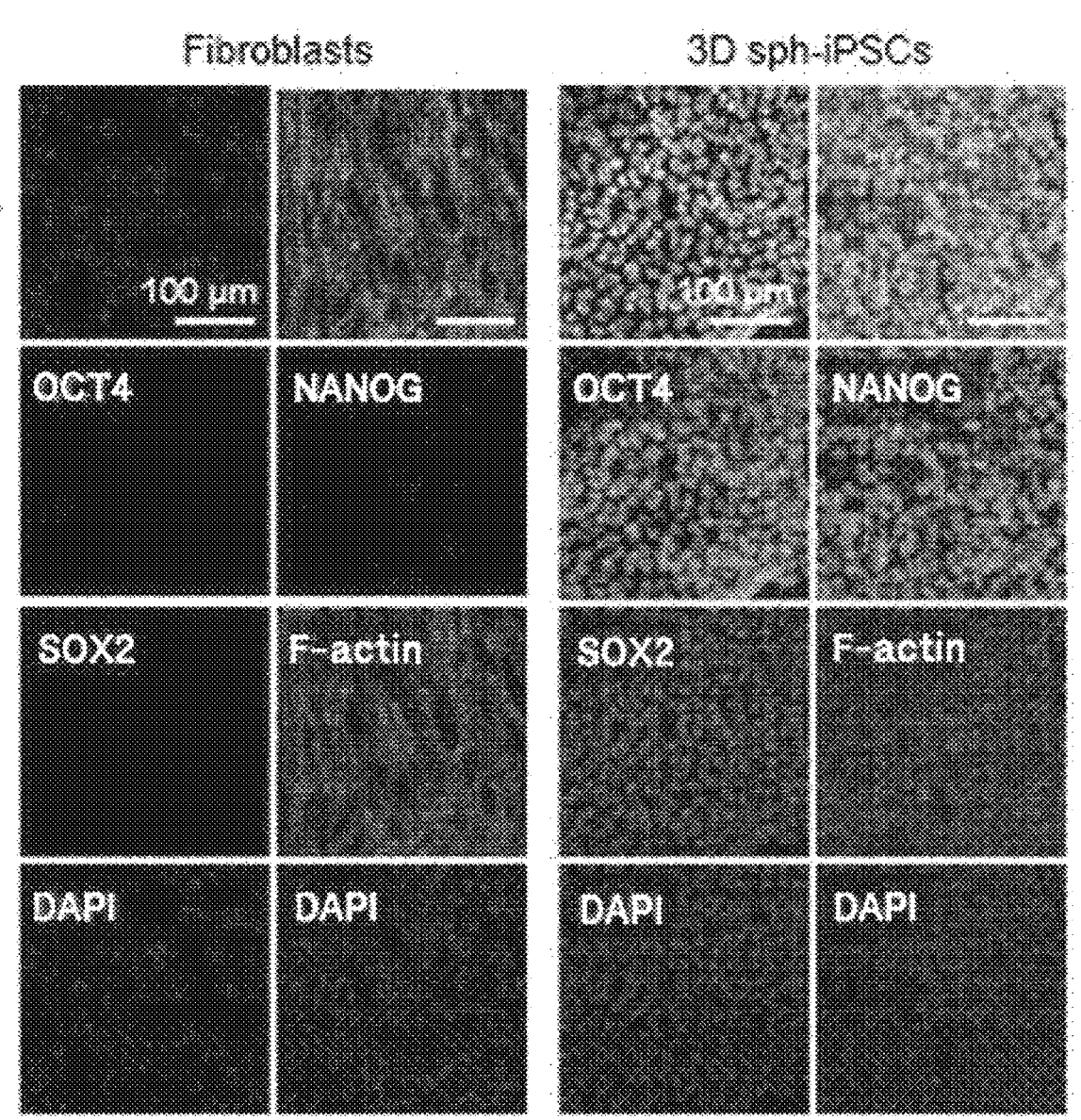

Referring to FIG. 9, it can be seen that the iPSCs produced according to the present invention have very high expression of pluripotency markers.

Example 4. Confirmation of Mass-Proliferation of Stem Cells

Figure 10:
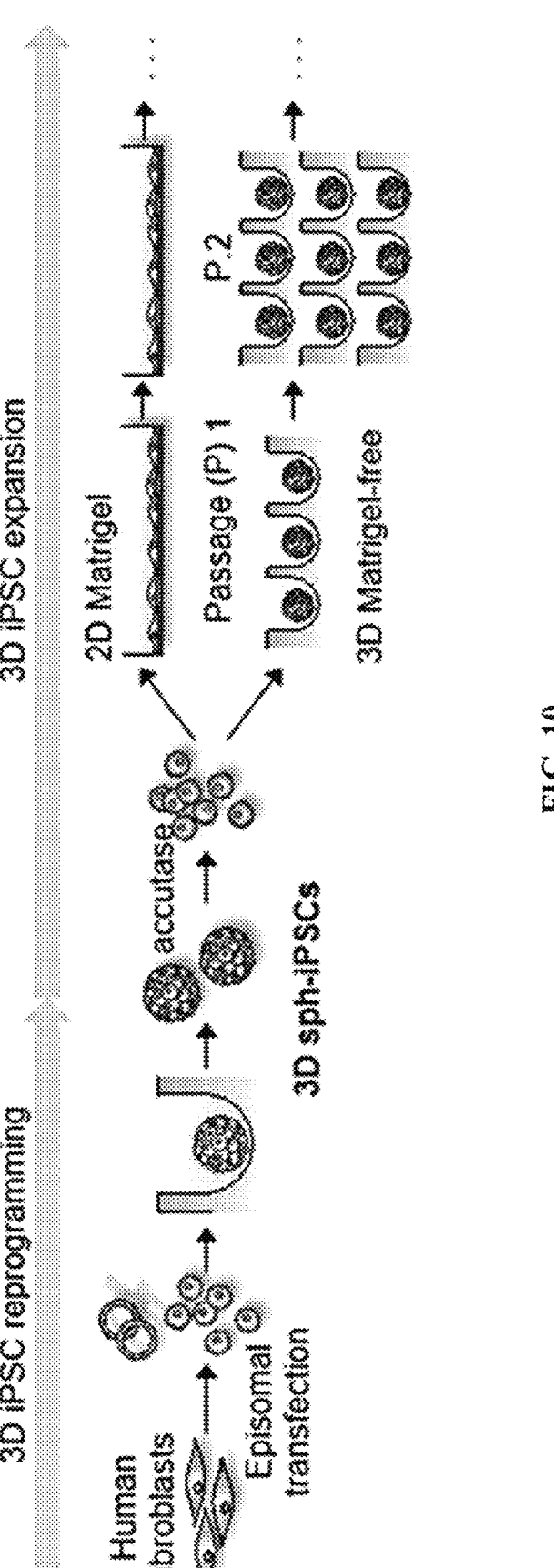
FIG. 10 is a schematic view illustrating the method of proliferating induced pluripotent stem cells according to an exemplary embodiment of the present invention and the comparative example.
Figure 11:
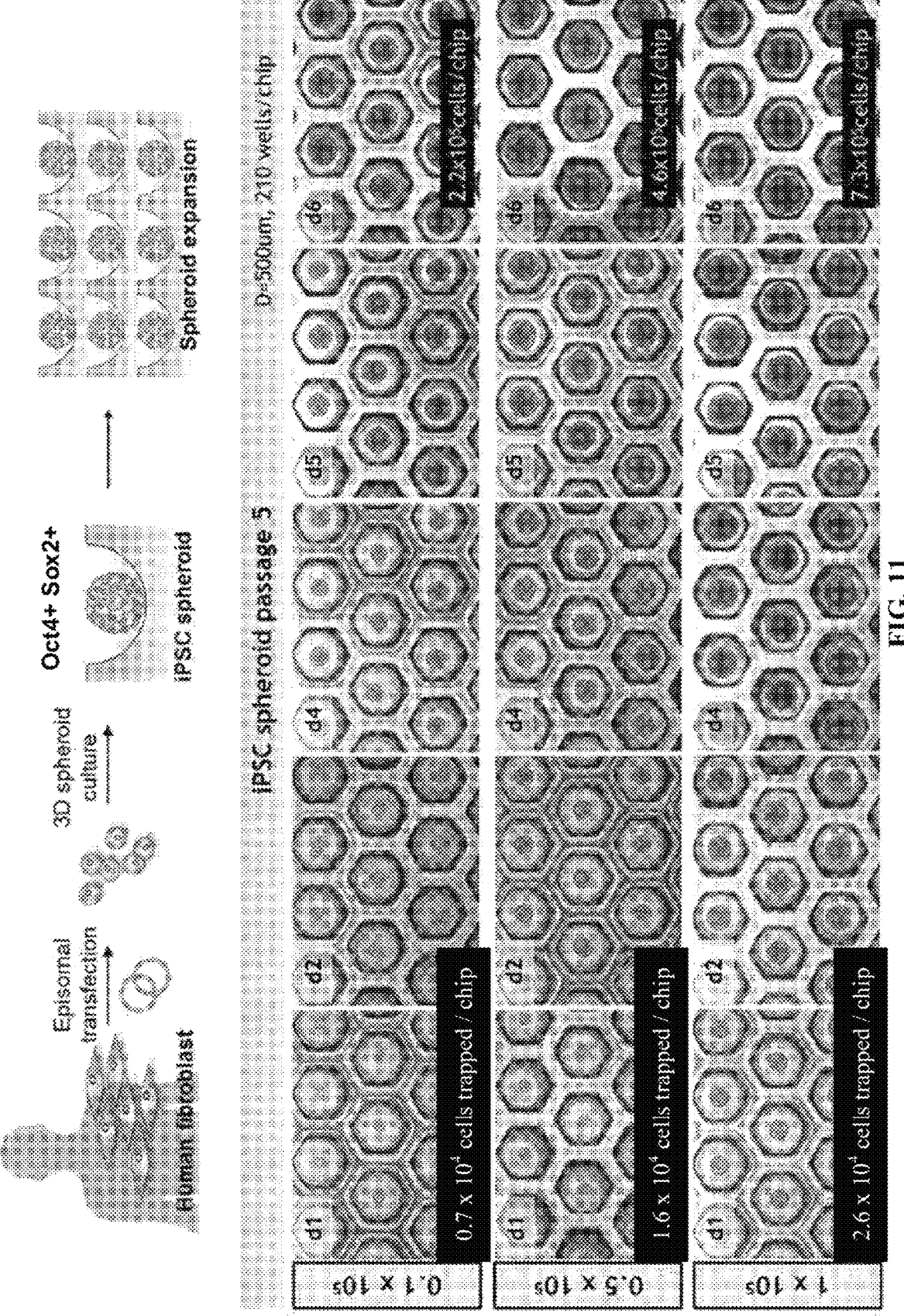
FIG. 11 is an image illustrating the process of proliferating induced pluripotent stein cells according to an exemplary embodiment of the present invention over time.
Figure 13:
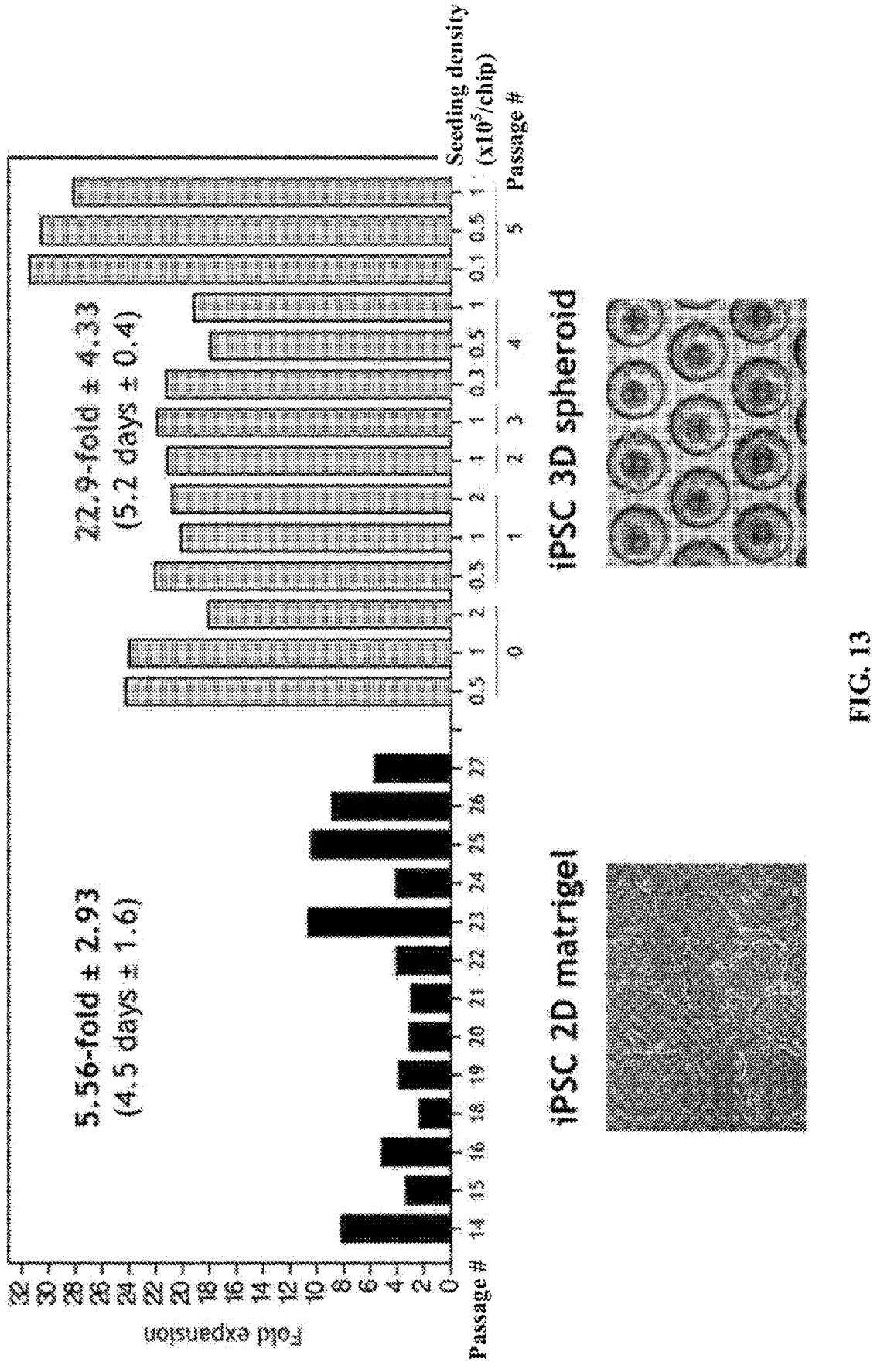
FIG. 13 is a graph comparing the proliferation efficiencies of an exemplary embodiment (3D cell culture) of the present invention and a comparative example (2D cell culture).
Figure 14:
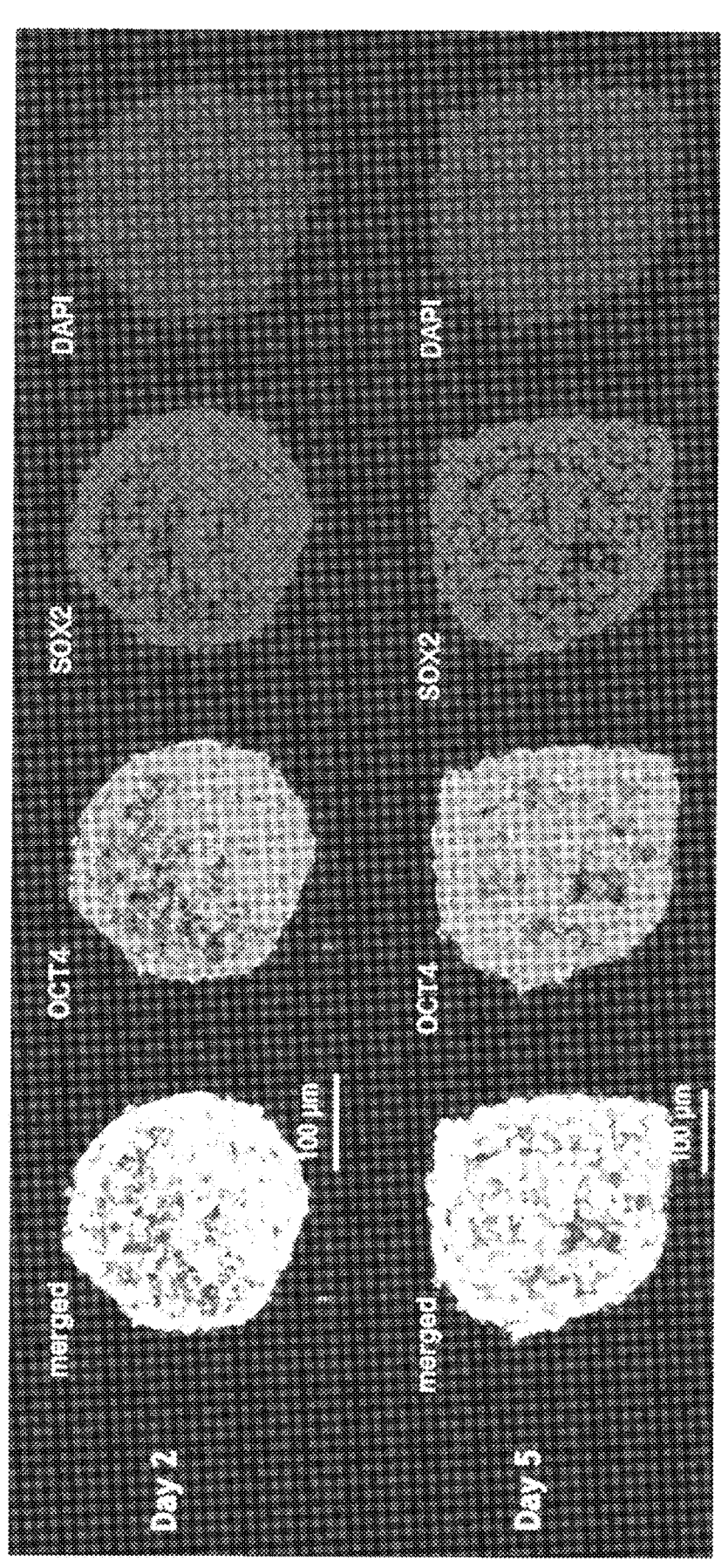
FIGS. 14 and 15 illustrate the results of pluripotency marker expression over the induced pluripotent stem cell proliferation time.
Figure 15:
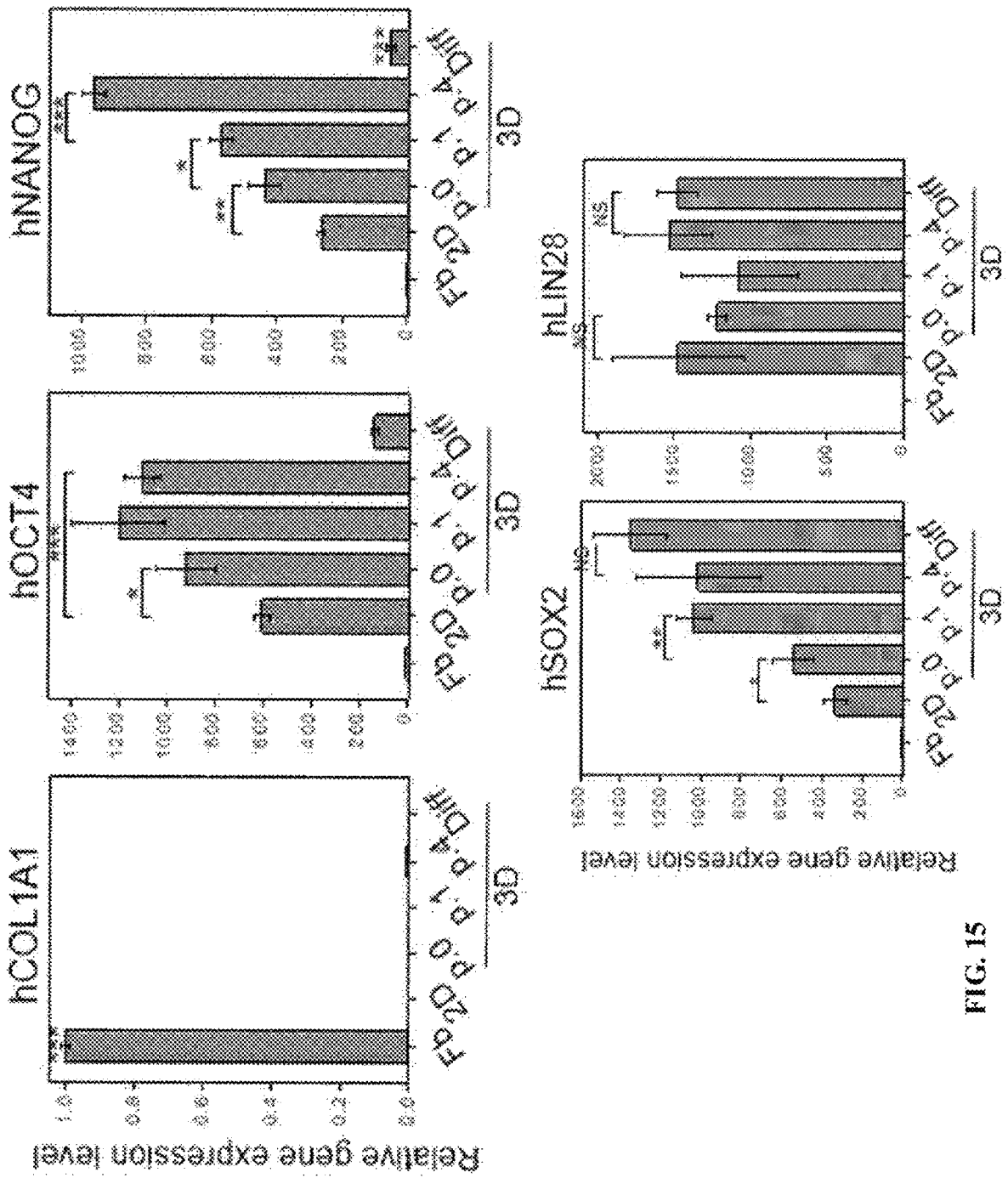

Referring to FIGS. 10 and 11, it can be seen that when the iPSCs produced by the present invention are subcultured, the iPSCs can be mass-proliferated. FIG. 13 is a graph comparing a proliferation efficiency when induced pluripotent stem cells reprogrammed in the 2D 12-well plate (coated with Matrigel, Comparative Example 1) are subcultured in a 2D Matrigel-coated plate with a proliferation efficiency when the induced pluripotent stem cells reprogrammed according to the example of the present invention are subcultured in the 3D subculture plate of the present invention. Referring to FIL 13, it can be seen that in the case of the present invention, the proliferation efficiency is increased by about 23 times. When making a determination in combination with the previous results in FIG. 12, it can be concluded that it is possible to mass-proliferate cells with a uniform size. Referring to FIGS. 14 and 15, it can be seen that the mass-proliferated iPSCs also have very high expression of pluripotency markers.

Figure 16:
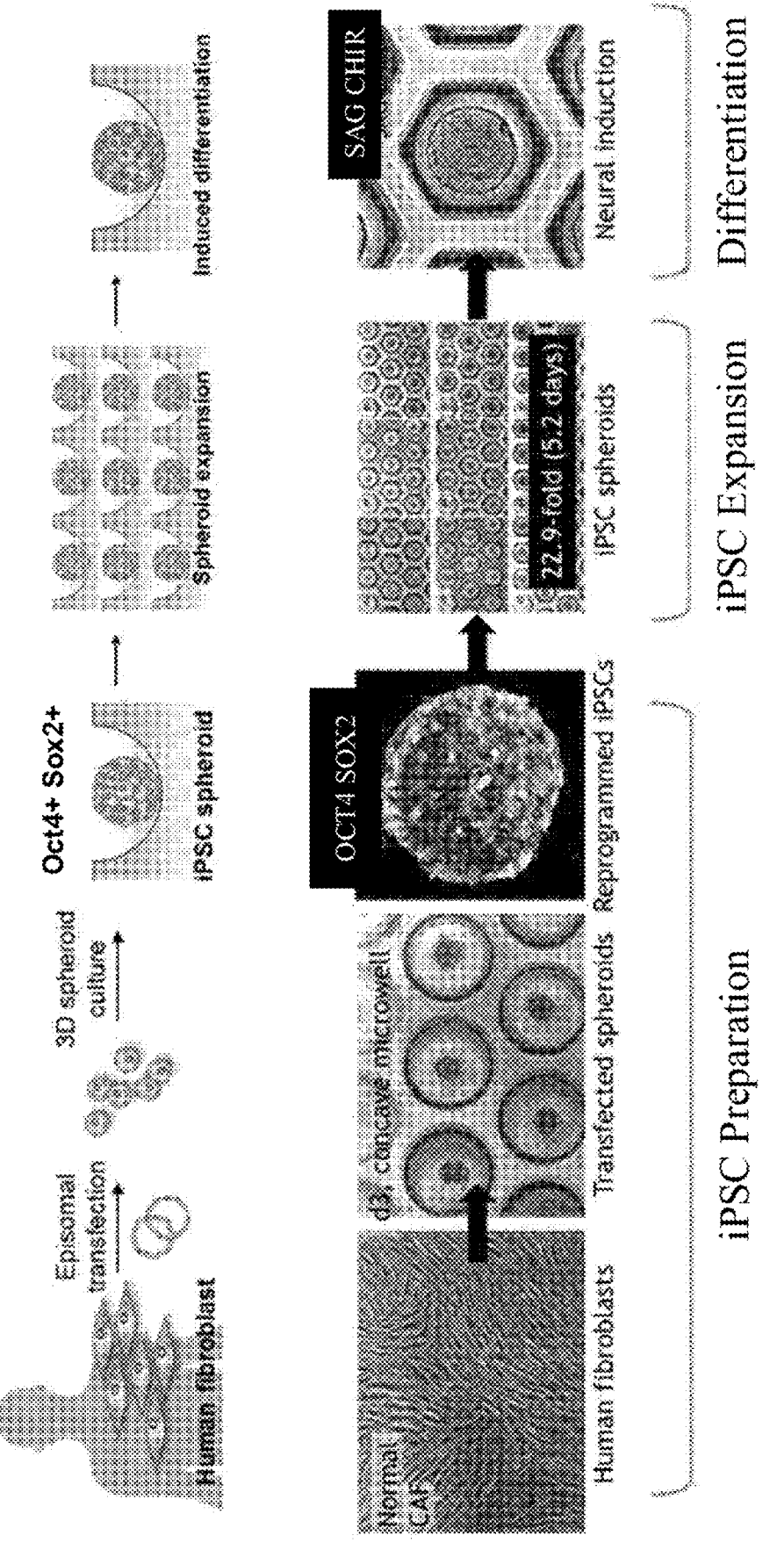
FIG. 16 schematically illustrates the process of production, proliferation and differentiation of induced pluripotent stem cells according to the present invention.

FIG. 16 schematically illustrates the present invention. When somatic cells are reprogrammed into induced pluripotent stem cells at high efficiency using the 3D cell culture plate of the present invention without using a hydrogel and spheroids of the reprogrammed induced pluripotent stein cells are separated and subcultured, the induced pluripotent stem cells may be mass-proliferated.

iPSCs are generated and proliferate in wells of the cell culture plate of the present invention. The iPSCs can also be stored as they are, and a medium can also be frozen at once. Since the well size can be adjusted without using a hydrogel such as Matrigel, a small amount of medium is used, and thus, the culture is economical. Moreover, the mass-proliferated induced pluripotent stem cells can be differentiated into various cells.

Although a specific part of the present invention has been described in detail, it will be obvious to those skilled in the art that such a specific description is just a preferred embodiment and the scope of the present invention is not limited thereby. Accordingly, the substantial scope of the present invention will be defined by the appended claims and equivalents thereof.

DESCRIPTION OF REFERENCE NUMERALS AND SYMBOLS

100: Well plate
101: Step
110: Main well
120: Sub well
121: Recessed part
130: Space part
140: Concave part
200: Connector for large-capacity and high-speed HCS
210: Base
220: Cover
240: Convex part

15

The invention claimed is:

1. A well plate comprising:

well structures having a repeating pattern;

each of the well structures is continuously provided with a space part in between a main well to be injected with a cell culture solution and a sub well including a recessed part where cells are cultured, wherein the recessed part is in a lowermost portion of the sub well;

wherein a step is in between the main well and the space part, and the sub well forms an angled surface relative to the space part.

2. The well plate of claim 1, wherein the step has an inclination angle ($\theta$1) ranging from 10 to 60° with respect to a wall of the main well.

3. The well plate of claim 1, wherein the angled surface has an inclination angle ($\theta$2) ranging from 30 to 80° with respect to a wall of the space part.

4. The well plate of claim 1, wherein the recessed part is provided in contact with the angled surface, the sub well has an upper end diameter ranging from 3.0 to 4.5 mm, the recessed part has an upper end diameter ranging from 0.45 to 1.5 mm, and a length ratio of the upper end diameter of the sub wells to the upper end diameter of the recessed parts ranges from 1:0.1 to 0.5.

5. The well plate of claim 1, wherein the main well has an individual volume ranging from 100 to 300 μl, the recessed part has an individual volume ranging from 20 to 50 μl, and an individual volume ratio of the main well to the recessed part is 1:0.1 to 0.5.

6. The well plate of claim 1, the space part has a height ($a_h$) ranging from 2.0 to 3.0 mm, the sub well has a height ($b_h$) ranging from 1.0 to 2.0 mm, and

a height ratio ($a_h$:$b_h$) of the space part to the sub well ranges from 1:0.3 to 1.

7. A 3D cell culture plate comprising:

the well plate according to claim 1; and a connector for large-capacity and high-speed high content screening (HCS) which supports the well plate, wherein the connector for high content screening (HCS) comprises a base attachable to and detachable from a lower end of the well plate, and a cover positioned on an upper portion of the well plate to be coupled to the base.

8. A 3D cell culture plate comprising:

the well plate according to claim 1; and a connector for large-capacity and high-speed high content screening (HCS) which supports the well plate, wherein the connector for high content screening (HCS) comprises a base and a cover positioned on an upper portion of the well plate to be coupled to the base.

9. The well plate of claim 1, wherein the step is angled and the space part is upright.

10. The well plate of claim 1, wherein a plurality of sub wells spaced apart from each other are provided within a single well structure.

11. The well plate of claim 1, wherein the recessed part is rounded.

12. The 3D cell culture plate of claim 7, wherein the recessed part collects spheroids and/or organoids.

13. A well plate comprising:

well structures having a repeating pattern;

each of the well structures is continuously provided with a space part in between a main well to be injected with a cell culture solution and a sub well including a recessed part where cells are cultured, wherein the recessed part is in a lowermost portion of the sub well;

wherein a step is in between the main well and the space part and the sub well forms an angled surface relative to the space part; and wherein a plurality of sub wells spaced apart from each other are provided within a single well structure.

* * * * *